US006770434B2

(12) United States Patent
Shvets et al.

(10) Patent No.: US 6,770,434 B2
(45) Date of Patent: Aug. 3, 2004

(54) BIOLOGICAL ASSAY METHOD

(75) Inventors: Igor Shvets, Dublin (IE); Dmitriy Kashanin, Dublin (IE); Dermot Kelleher, Dublin (IE); Vivienne Williams, Dublin (IE); Yuri Volkov, Dublin (IE)

(73) Assignee: The Provost, Fellows and Scholars of the College of the Holy & Undivided Trinity of Queen Elizabeth Near Dublin, Dublin (IE)

( * ) Notice: Subject to any disclaimer, the term of this patent is extended or adjusted under 35 U.S.C. 154(b) by 0 days.

(21) Appl. No.: 09/750,348

(22) Filed: Dec. 29, 2000

(65) Prior Publication Data

US 2002/0086329 A1 Jul. 4, 2002

(51) Int. Cl.[7] ................................................. C12Q 1/00
(52) U.S. Cl. ............................................. 435/4; 422/58
(58) Field of Search ................................ 435/4, 287, 2, 435/287.9; 422/58, 63, 100, 101, 102, 104

(56) References Cited

U.S. PATENT DOCUMENTS

| | | |
|---|---|---|
| 4,727,019 A | 2/1988 | Valkirs et al. |
| 4,912,037 A | 3/1990 | Lemonnier |
| 4,912,057 A | 3/1990 | Guirguis et al. |
| 5,284,753 A | 2/1994 | Goodwin, Jr. |
| 5,302,515 A * | 4/1994 | Goodwin, Jr. ............... 435/29 |
| 5,514,555 A | 5/1996 | Springer et al. |
| 5,543,327 A | 8/1996 | Yen-Maguire et al. |
| 5,556,752 A | 9/1996 | Lockhart et al. |
| 5,571,410 A | 11/1996 | Swedberg et al. |
| 5,578,492 A | 11/1996 | Fedun |
| 5,601,997 A | 2/1997 | Tchao |
| 5,645,988 A | 7/1997 | Vande Woude et al. |
| 5,670,113 A | 9/1997 | Akong et al. |
| 5,679,526 A | 10/1997 | Buechler et al. |
| 5,723,345 A | 3/1998 | Yamauchi et al. |
| 5,932,100 A | 8/1999 | Yager et al. |
| 5,939,272 A | 8/1999 | Buechler et al. |
| 5,985,579 A | 11/1999 | Buechler et al. |
| 5,998,160 A | 12/1999 | Berens |
| 6,042,709 A | 3/2000 | Parce et al. |
| 6,042,837 A | 3/2000 | Kalland et al. |
| 6,063,589 A | 5/2000 | Kellogg et al. |
| 6,103,479 A | 8/2000 | Taylor |
| 6,113,768 A * | 9/2000 | Fuhr et al. .................. 204/643 |
| 6,287,765 B1 * | 9/2001 | Cubicciotti ..................... 435/6 |

OTHER PUBLICATIONS

Steel Adam. The Flow Thru Chip: A three Dimensional Biochip Platform. Microarray Biochip Technology. Eaton Publishing, Mass, 2000, pp. 87–117.*

* cited by examiner

*Primary Examiner*—Ralph Gitomer
(74) *Attorney, Agent, or Firm*—Birch, Stewart, Kolasch & Birch, LLP

(57) ABSTRACT

Biological assays using various constructions of biochips are disclosed to mirror in vivo situations. The biochip 50 comprises a microchannel 51 having a liquid outlet port 1, bubble release port 2 and a liquid outlet port 3 with an associated bubble release port 4. A multiplicity of tests can be performed often by coating the bore of the microchannel 50 which various adhesion mediating proteins or the use of chemoattractants. The assay assembly 60 comprises a syringe pump feeding the biochip 50. An inverted microscope 65, digital camera 66 and recorder 67 are provided. A sample liquid containing cells in suspension is injected slowly through the biochip and the effect of the assay recorded over a long period.

39 Claims, 26 Drawing Sheets

# BIOLOGICAL ASSAY METHOD

BACKGROUND OF THE INVENTION

Field of the Invention

The present invention relates to a biological assay and a biological assay apparatus.

Biochemical, microbiological, chemical and many other assays are being performed every day in laboratories. While a considerable amount of attention has naturally been placed on such biological cell assaying for humans, this is also be becoming more important in the field of animal welfare and indeed plant production generally.

A rapidly advancing research area in biology is the study of cell receptor-ligand interactions resulting in cell-substratum and cell-cell adhesion followed by subsequent cell migration. The pre-requisite to transendothelial migration of certain cell lines into sites of infection is paramount to the study of inflammatory diseases. This can be briefly summarised as cell flow and rolling, tethering and activation of integrin receptors which is a key recognition step, attachment to the endothelial ligands via activated integrins and finally transendothelial migration or diapedesis. Unfortunately, to date, most of the assay techniques are not particularly successful for the study of these mechanisms. Currently, the majority of studies involving cell rolling and chemokine induced cellular arrest have utilised capillary systems wherein cell flow and shear stress are controlled utilising syringe pumps. Such observations are constrained by a number of factors. Firstly, the relative large (>100 μm) size of the standard glass capillaries limits the physiological analogies to the proximal microvascular regions. Secondly, such studies can only be utilised to study single end-points and cannot be utilised to examine cell choices in migration Thirdly, optical aberrations related to the spherical geometry of the glass capillary sections limit stage-related in situ (post-fixation) analysis of the intracellular structures (cytoskeleton and signalling molecules). Finally and most importantly, the usual observation periods lie between 5–30 minutes for rolling experiments. Longer studies are required to study subsequent crawling steps on endothelial and extra-cellular matrix ligands. In this regard, studies relating to the effects of chemokines have largely been limited to cellular arrest on adhesion receptor ligands and have not been extended to the study of cell crawling. For example, specific chemokines have been shown to induce rolling arrest with enhanced binding of lymphocytes to ICAM-1, otherwise known as CD54.

Presently accepted techniques for cell adhesion or binding assays involve the initial coating of a surface of a device with a substrate, typically a protein. Cells are deposited onto the substrate and allowed to settle. Following the settling of the cells, the device is placed on a heating stage at 37° C., which is attached to an inverted microscope for visual analysis, or alternatively to a stand-alone heating stage and progression of cell binding can be checked at intervals with the inverted microscope. The duration of these assays may be varied depending on the cell line and choice of substratum. Following cell adhesion, free cells may be washed away and a subsequent cell count may be carried out.

Although these methods provide us with semi-quantitative information regarding a cell type's affinity for a particular substratum, there is no simple method for quantitative characterisation of binding or methods enabling a prolonged study of cell rolling, the ensuing capture by the substratum and subsequent attachment. Furthermore, direct studies of changes in cell morphology, cell growth and biochemical changes cannot be provided easily with these techniques since, determining the kinetics of attachment and resulting morphological changes requires multiple replicated experiments being analysed at different times.

DESCRIPTION OF PRIOR ART

U.S. Pat. No. 5,998,160 (Berens et al) describes a static assay which unfortunately does not have any consideration of cell flow and rolling.

The ability of T-cells circulating in the bloodstream to adhere to the endothelium, switch to a motile phenotype and penetrate through the endothelial layer is recognised as a necessary requirement for the effective in vivo movement or as it is sometimes referred to, trafficking of specific lymphocyte sub-populations. Motility assays are done in combination with attachment assays since following adhesion; cells are expected to switch to the motile phenotype. Motility assays are assessed by estimating the ratio of cells undergoing cytoskeletal rearrangements and the formation of uropods (extension of the trailing tail). One of the major disadvantages of this and the previous adhesion assays is the geometrical design (microscope slides and multiple well chambers), which does not at all resemble the in vivo situation.

The most commonly used cell transmigration assay is a modified "Boyden chamber" assay such as described in U.S. Pat. No. 5,578,492 (Fedun et al). This involves assessing the crossing of a quantity of cells through a microporous membrane under the influence of a chemoattractant, recombinant or cell-derived. Here the diameter of the micropores are less than the diameter of the cells under investigation, such that the cells must deform themselves in order to squeeze through the pores thereby constructing an analogy to the transendothelial migration of cells in physiological circumstances. Once the cells are deposited onto the membrane, the chamber can be incubated for intervals over time at a suitable temperature, usually 37°. Following this, the bottom chamber or opposite side of the top chamber may be analyzed for cells that have squeezed through the microporous membrane.

U.S. Pat. No. 4,912,057 (Guirguis et al), U.S. Pat. No. 5284753 (Goodwin et al), U.S. Pat. No. 5,302,515 (Goodwin et al), U.S. Pat. No. 5,514,555 (Springer et al) and U.S. Pat. No. 5,601,997 (Tchao) are typical examples of these assays. The main disadvantage of the assays described in those specifications is that the biological process of transmigration through the micropores is difficult to observe due to the geometrical configuration of the apparatus involved. The lens of the optically inverted microscope must be able to focus through the lower chamber and the microporous membrane. This obviously leads to difficulties due to optical aberrations. In effect, the study of the cells morphology changes while transmigrating across the membrane and their subsequent cytoskeletal changes reverting to their former state is a process which is difficult to monitor and record due to limitations with current techniques. In addition, although it is possible to alter such an experiments parameters following the initiation of the experiment, such as the introduction of a second chemoattractant, recombinant or cell-derived, at some specified time after commencing the experiment, it is not possible to distinguish separate effects from each said chemoattractant.

In addition to cell biology studies, the pharmaceutical industry has major problems in the drug screening process and while high throughput screening (HTS) has been extremely successful in the elimination of the large majority of unsuitable drugs, it has not progressed beyond that and usually, after a successful HTS assay, a pharmaceutical company may still have 7,000 possible drugs requiring assessment. This requires animal trials and anything that can be done to reduce the amount of animal trials is to be desired. Thus, there is a need for new techniques for drug testing in the pharmaceutical industry. The current proposals are to screen the physiological response of cells to biologically active compounds such as described in U.S. Pat. No. 6,103,479 (Taylor). This again, unfortunately, is still a static test. Since the cells are spatially confined with the drug, there may be a reaction but it may not necessarily take place when the cells are free to flow relative to the drug as in, for example, the microcapillaries of the body. There are other disadvantages such as the transport and subsequent reaction of the drug following its injection into the animal. Probably the most important disadvantage is that it does not in any way test, in a real situation, drug efficacy.

Finally, there are no techniques at the present moment for performing assays to test the interaction of a large number of chosen compounds with living cells while the cells or compounds mimic the in vivo situation of continuous flow.

While in the description herein, the examples all refer to animal cells and indeed mainly human cells, the invention equally applies to plan cells. The term "sample liquid" refers to a suspension of living cells within a suitable carrier liquid which is effectively a culture medium. More than one cell type may be in suspension. Further, the term "reagent liquid" could be any liquid from a drug under assessment, a poison, a cell nutrient, chemoattractant, a liquid containing other cells in suspension or indeed any liquid who's effect the sample liquid requires assessment.

The present invention is directed towards providing such methods and apparatus for performing such assays.

SUMMARY OF THE INVENTION

The present invention provides a biological assay method comprising:

delivering a sample liquid of a suspension of cells at a controlled steady flow rate through a biochip in the form of an elongate enclosed microchannel;

causing an externally generated test to be carried out on the sample liquid as it is being delivered through the biochip; and examining the sample liquid over time to observe the effect of the test on the sample.

The externally generated test can be carried out in many ways, for example, it can comprise coating the internal bore of the biochip with a protein which could, for example, be an extracellular matrix ligand or could be formed by an endothelium layer which in turn would be formed by seeding the biochip with endothelial cells allowing the cells to grow on the walls. The cells can be taken from an animal or indeed most often from a human, but could also be from a plant. The bore of the biochip, in certain tests, is substantially the same size as the post capillary venules of an animal or, more particularly, a human. With such a method, for example, one can have tests for cell flow, rolling, tethering and migration of previously adhered cells, and adhesion. All of these may be recorded in any suitable manner. It is envisaged that the velocity of the delivery of the sample liquid may be varied to provide different test conditions or the velocity of the delivery of the sample liquid can be increased until previously adhered tests are removed and then the velocity forms a measure of the adherence. Alternatively, a separate flushing liquid may be introduced to remove previously adhered cells, the velocity of the flushing liquid forming a measure of the adherence. Needless to say, after cells have been adhered to the protein, the sample liquid could be replaced by a reagent liquid and the effect of the reagent liquid could be observed. The reagent liquid could be any suitable liquid. One could be, for example, an adhesion detachment reagent liquid and thus the effect of this on the previously adhered cells could be monitored. Needless to say, any reagent liquid may be delivered simultaneously with the sample liquid through the biochip to achieve various tests. For example, it would be possible to deliver a reagent liquid at a controlled steady flow rate through another microchannel connected to the first microchannel, the channels being connected intermediate their ends by an interconnecting channel. The fluid pressure of the liquids could be chosen so as to cause a diffusion of the reagent through the interconnecting channel or alternatively the fluid pressures could be maintained equal to prevent diffusion of the reagent. Similarly, the channels may be connected intermediate their ends by an interconnecting channel having a restricted entry throat, which restricted entry throat would preferably have a cross sectional area less than that of a cell when the cell is freely suspended in the sample liquid. This would be a very good way of studying the mechanisms involved in cell migration from the endothelium to the extracellular matrix.

In other embodiments, the bore of the microchannel could be provided with a hydrophobic coating such as liquid silicon.

It is envisaged that more than one cell type may be held in suspension as this often happens in practice and indeed in many instances, it may be advantageous to deliver a reagent liquid and a sample liquid through the microchannel to form multilaminar flow and then if the reagent liquid comprises a chemoattractant suitable for one of the types of the cell, it will be possible to effectively separate that particular type of cell from the sample.

Further, the invention envisages a method in which the biochip comprises two microchannels, one a feeding microchannel having a cell reservoir intermediate its ends and the other a reactant microchannel connected to the reservoir by a connecting means comprising:

storing cells in the cell reservoir;

feeding and growing the cells in the cell reservoir by delivering a culture medium through the feeding microchannel; and delivering reagent liquid through the reactant microchannel.

The reagent liquid could, for example, be one or more of a chemoattractant, toxic substance or pharmaceutical preparation and these could be recombinant or cell derived.

It is envisaged that a plurality of tests can be carried out simultaneously using the one sample liquid forming portion of a large sample and using different test conditions or alternatively, a plurality of the same tests may be carried out using different sample liquids and the same test conditions.

According to the invention, there is provided a biochip comprising:

an elongate main microchannel;

an inlet port mounted on the proximal end of the main microchannel;

an outlet port adjacent its distal end;

a separate liquid feeder microchannel connected to the main microchannel, the feeder microchannel having an inlet port; and an outlet feeder port connecting the feeder microchannel and the main microchannel.

Ideally, the outlet port between the feeder microchannel and the main microchannel has a restricted throat. Further, there can be produced a biochip comprising two separate main microchannels and a connecting microchannel connecting the two separate main microchannels. Such separate microchannels can be parallel, diverge towards each other and indeed the connecting channel may also have a restricted throat or the channel itself may just have a restricted cross section.

Further, there is provided a biochip comprising:

two separate main microchannels; and a common microchannel connected to the two main microchannels to provide an extension of the two main microchannels.

This common microchannel can feed two further microchannels and indeed the microchannel can comprise a main microchannel and a take-off microchannel intermediate its ends, the take-off microchannel having an entrance which projects into the main microchannel to divert flow from the main microchannel into the take-off microchannel. Further, a microwell can be incorporated in a microchannel forming part of a biochip, which microwell may have connected to it a further feeder microchannel delivering into and out of the microwell, the feeder microchannel having an inlet port adjacent its proximal end and an outlet port adjacent is distal end.

It is envisaged that the microchannel according to the present invention will generally have a planar top wall to allow good optical properties for examination under a microscope and generally speaking, the microchannel comprises planar top, bottom and side walls which side walls taper outwards and upwards away from each other. Ideally, the top wall is removable and is formed from a plastics film.

Preferably, each port has a bubble release port and valve associated therewith. The cross sectional area of the microchannel is between 25 $\mu m^2$ to 10,000 $\mu m^2$ and preferably greater than 400 $\mu m^2$.

It is envisaged that assemblies comprising a plurality of biochips as described above will be formed on the one base sheet and will preferably have various common feeder microchannels having ports therein. The advantage of a whole lot of biochips all on the one sheet is that they can be readily easily examined by the one microscope.

BRIEF DESCRIPTION OF THE DRAWINGS

The invention will be more clearly understood from the following description thereof, given by way of example only, with reference to the accompanying drawings, in which.

DETAILED DESCRIPTION OF THE PREFERRED EMBODIMENTS

Figure 1:
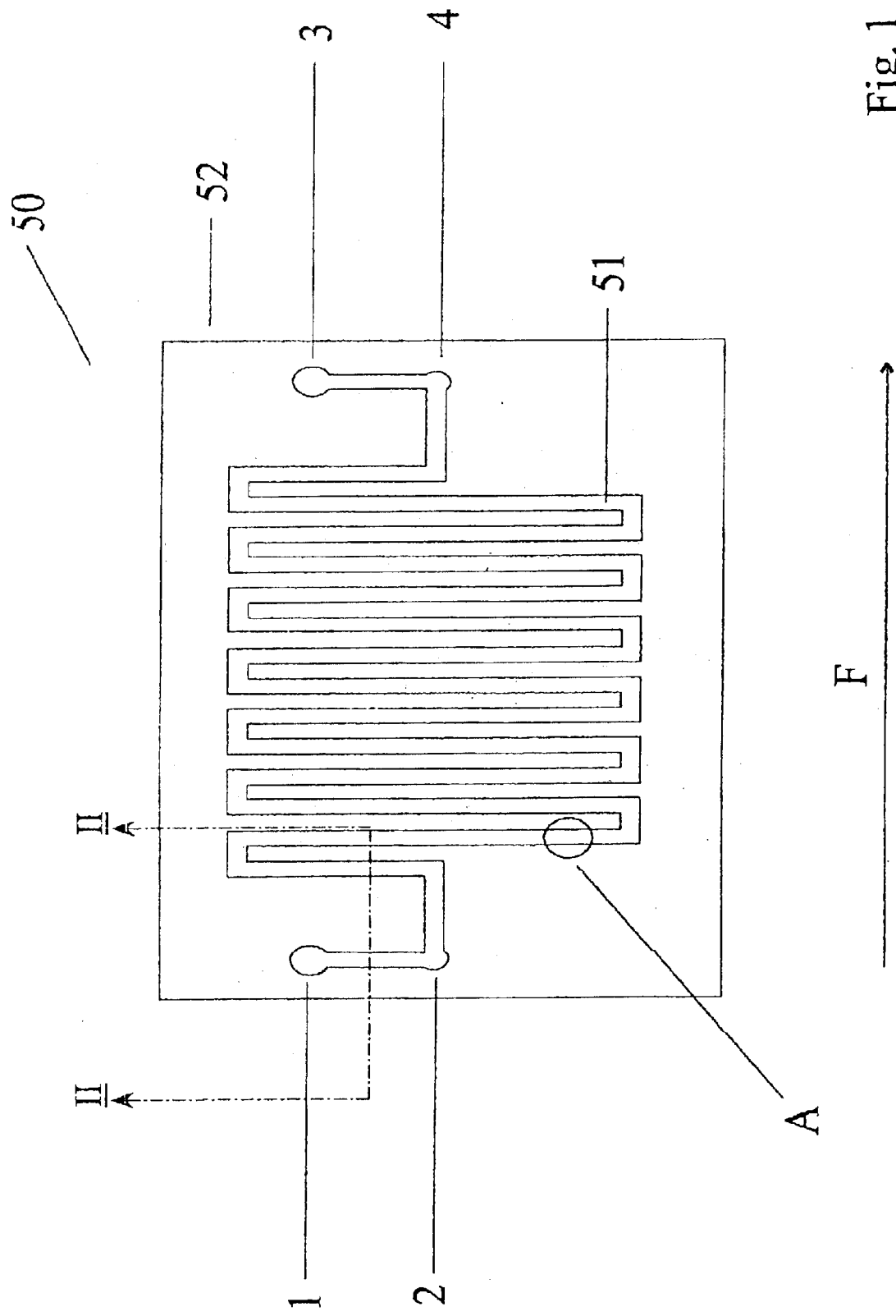
FIG. 1 is a plan view of a biochip according to the invention.

In the drawings, there are described many microfabricated biochips having a plurality of ports which it would be very confusing to identify by different reference numerals in the drawings of each microchip or biochip. Thus, all the ports in the drawings are identified by the reference numerals 1 to 40. Accordingly, in certain circumstances, an outlet port will be identified by the reference numeral 4 and in another embodiment, it may be an inlet port. However, for clarity in viewing the drawings, this scheme of identification has been adopted.

Figure 2:
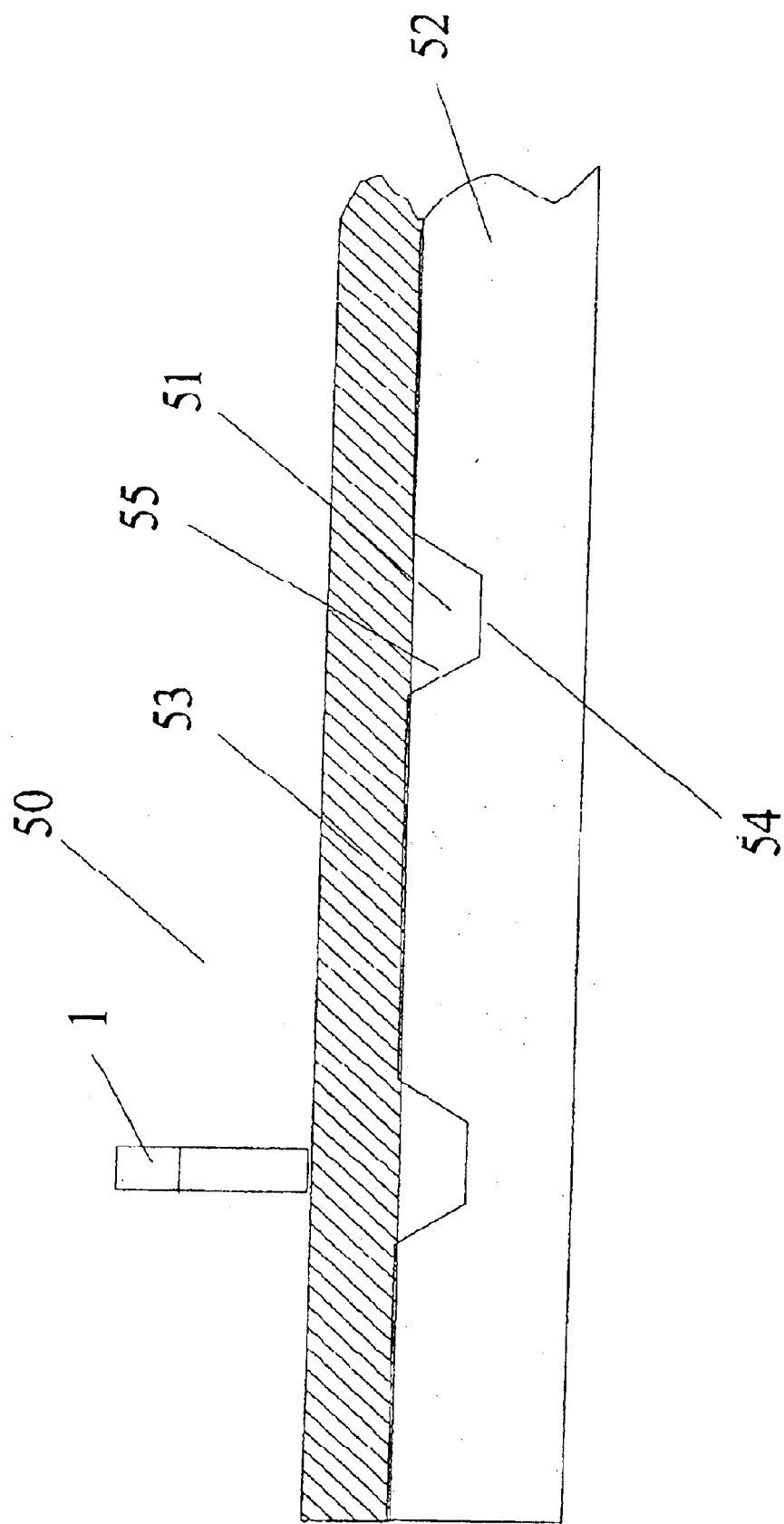
FIG. 2 is a sectional view along the lines II—II of FIG. 1.

Referring to FIGS. 1 and 2, there is illustrated a biochip, indicated generally by the reference numeral 50 comprising a microchannel 51 formed in a base sheet 52. The microchannel 51 comprises a top wall 53 formed from plastics film and has a planar bottom wall 54 and tapering side walls 55 which taper outwardly away from the bottom wall 54. A fluid inlet port 1 is illustrated in FIG. 2. The biochips 50 are fabricated using standard lithographic and hot embossing techniques. A stainless steel substrate is masked with photoresist (SU-8-5 m, as distributed by Chestech). After ultraviolet lithography, the photoresist mask is delivered and the substrate is electrochemically etched to produce a negative master mould in stainless steel. The remaining mask is subsequently removed. Hot embossing is employed to replicate the microfluidic pattern of the microchannels 51 in a variety of thermoplastic materials such as PMMA, polycarbonate, and polystyrene. The liquid inlet and outlet ports, such as the port 1, are glued in position. The biochip is treated in oxygen plasma (0.1 torr, 80% oxygen and +100V for 30 seconds) to ensure a hydrophilic surface and is subsequently sealed with a pressure-sensitive film (PHARMCAL PM-150-c TC-249 V-232C 150 POLY H9, manufactured by Flexcon). This film is a 1.5 mil top-coated clear polyester film, coated with a permanent adhesive containing a photoluminescent additive, backed with a 1.5 mil polyester release liner. The width of the channels may vary from 20–100 $\mu$m and a depth from 20–40 $\mu$m. The biochip 50 is thus an optically transparent structure. The biochip 50 illustrated in FIG. 1 has a liquid inlet port 1, a bubble release port 2 incorporating a bubble release valve, an outlet port 3 and a bubble release port 4 associated with the outlet port 3.

It will be appreciated that to a certain extent, the term "input port" and "output port" is a misnomer since in one circumstance, a port may operate as an input port and in another circumstance, as an output port. The size of the microchannels can vary in cross section from between 5 $\mu$m×5 $\mu$m to 100 $\mu$m×100 $\mu$m but will generally exceed 20 $\mu$m×20 $\mu$m.

Figure 3:
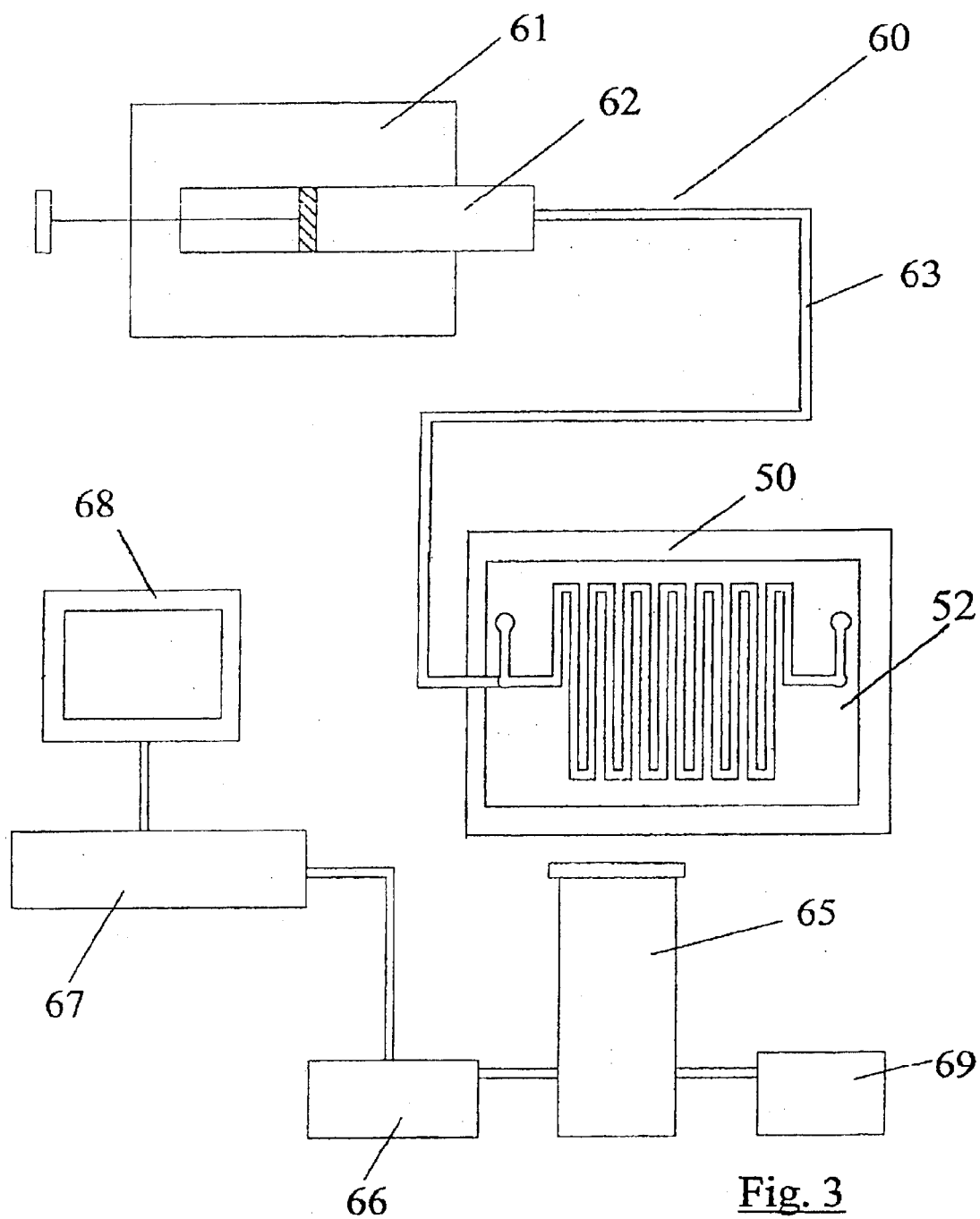
FIG. 3 is a diagrammatic view of an assay assembly according to the invention.

Referring to FIG. 3, there is illustrated an assay assembly, indicated generally by the reference numeral 60, comprising a pump assembly 61 incorporating a syringe pump 62 feeding by means of conduit 63 the biochip 50. An optically inverted microscope 65, connected to a digital camera 66, a recorder 67 and monitor 68 are mounted beneath the biochip 50. An epifluorescence device 69 is also connected to the microscope 65. It will be appreciated that the epifluorescence device 69 may not always be required.

Figure 4:
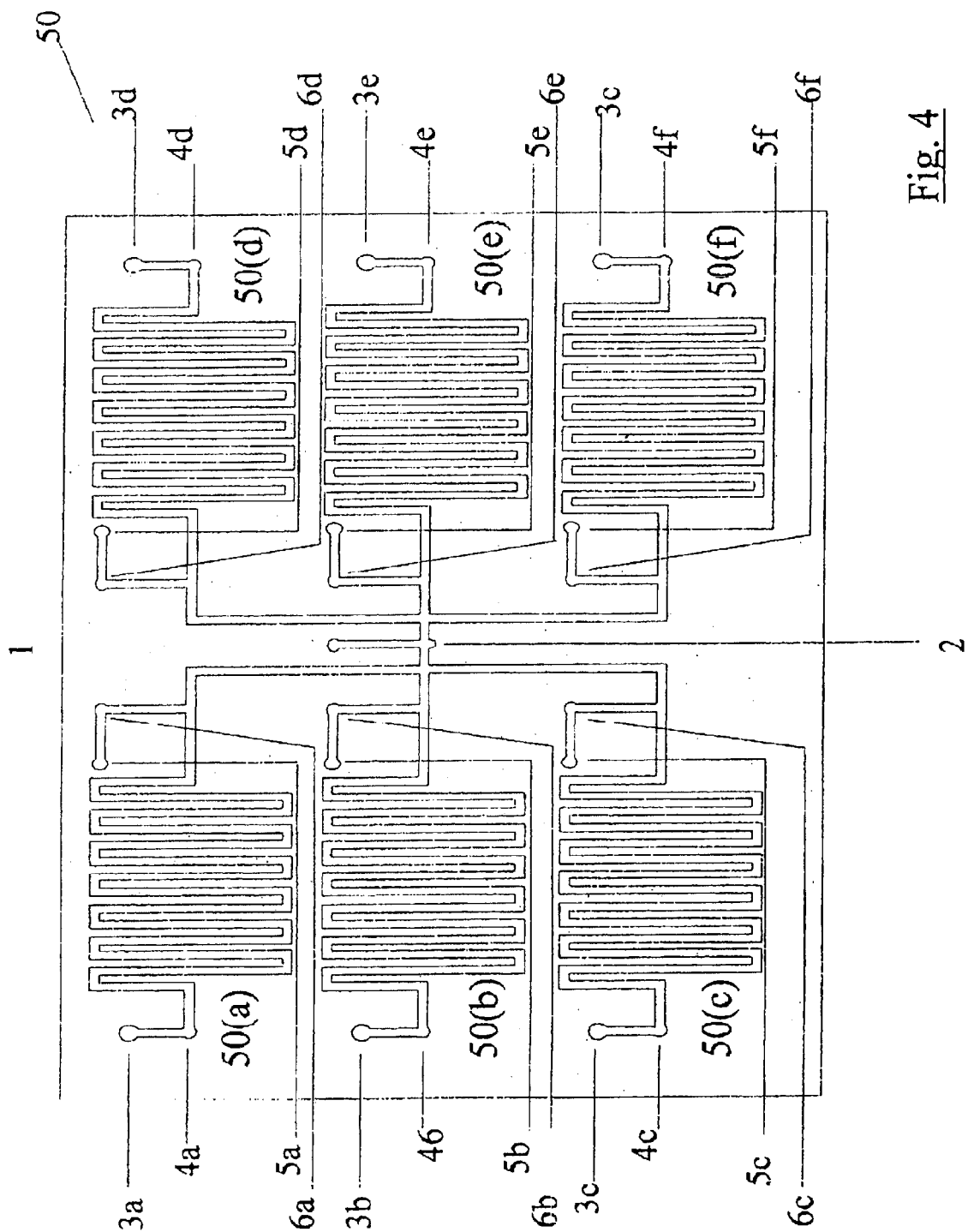
FIG. 4 is a plan view of a biochip assembly utilising the biochips of FIG. 1.

Referring now to FIG. 4, there is illustrated a biochip assembly, indicated generally by the reference numeral 70 comprising six biochips 50, identified by the subscripts (a) to (f) with inlet ports 1, 5, 9, 13, 17 and 21, as well as corresponding outlet ports 3, 7, 11, 15, 19 and 23. It will be noted that each biochip 50 is connected by a further microchannel to an inlet port 25 having a bubble-release port 26 associated therewith. The apparatus described has been used in accordance with the invention to observe and study the flowing and rolling of cells for up to several hours. Various other assays as will be described hereinafter have been carried out, including the transmigration of cells on endothelial ligands or extracellular matrix ligands through a constricted channel. The use of image acquisition and recognition software for observation and data collection, including automatic optical readouts, can be provided and is not described as such apparatus and schemes are well known in the art. The number of biochips forming a biochip is a matter of choice.

In many instances, for ease of reference and to avoid a multiplicity of numerals, 51 usually identifies a microchannel and where there is more than one microchannel, subscript letters are used.

One of the great advantages of the assay assembly 60 that will become apparent is that a variety of tests can be carried out. However, there is a further advantage in that since these tests occur over relatively long periods of time, of the order of hours or so, it is possible to use the one microscope to carry out a multiplicity of examinations as it is usually only necessary to have the activities recorded at discrete time intervals. Thus, for example, the microscope can be indexed to examine each of the biochips 50(a) to 50(f) by simple manipulation. Further, it will be appreciated that assemblies with greater than six separate biochips mounted thereon, may be advantageous. By using relatively large assay assemblies, that is to say, containing a multiplicity of individual biochips and using the one microscope, it should be possible to carry out a multitude of assays at the same time.

The present examples relate mainly to cell assays of humans and the cells were contained in the solution of culture medium all maintained at 37° C. It is well known that there are some essential nutritional requirements for living human cells and standard culture medium was used. A minimal medium contained glucose as a source of carbon, $NH_4Cl$ as the source of nitrogen and salts such as $Na^+$, $K^+$, $Mg^+$, $Ca^+$, $SO_4^{2-}$, $Cl^-$ and $PO_4^{3-}$. In certain circumstances, in carrying out the tests, when a richer culture medium was required, partly hydrolysed animal or plant tissues rich in amino acids, short peptides and lipids, were used, as well as yeast extract which is rich in vitamins and enzyme cofactors, nucleic acid precursors and amino acids.

One of the major difficulties in carrying out an assay according to the present invention is to ensure that the flow rate was kept as constant as possible. The problem with variations in flow rates is that they can provide variations in the shear stress on the wall, for example, of a capillary or of a microchannel such as in accordance with the present invention. Typical flow rates in the assays were in the range from 100 pl/min to 10 $\mu$l/min. The corresponding linear velocities for these flow rates were 0.5 $\mu$m/s to 5 cm/s respectively.

In the assays now being described, the microchannels were comparable in size to the post capillary venules in the human bodies and therefore it is suggested that the microchannels imitate the natural environment more closely than any other form of channel. Thus, when dealing with assays concerning venules in the human body, sizes are of the order of 20 $\mu$m while for human capillaries, they can be as small as 8 $\mu$m. In the embodiments already described, each port has associated therewith a bubble-release port. This is vital because bubbles in the microchannel structures effectively result in the termination of an assay and therefore cannot be allowed. Initially upon injection into a microchannel of a biochip, the only port that will be open is the bubble-release port. It has been found that the channel connecting the input or output port to the bubble-release port must be wider than the microchannels in the rest of the structure. The reason for this is that during pressure build-up, the fluid containing bubbles will be released through the wider channel connected to the bubble-release port and not through the microchannels of the remaining structure where the assay will be carried out. Following the release of these bubbles, the bubble-release port is closed and the fluid then flows throughout the microchannel structure. Finally, the length of the microchannel is varied depending on the test being carried out.

As mentioned already, a pressure-sensitive film is used to cover the biochip effectively sealing the microchannels. Thus, the pressure-sensitive film can be removed after the execution of an assay and accordingly it is possible, prior to removal of the film, to inject a solution which fixes cells to the film and the plastic substrate of the biochip enabling further study. The pressure-sensitive film may obviously be removed and the cells taken away for additional research.

Referring to FIGS. 1 and 2, to study the flow, rolling and migration of cells, a ligand, namely, an adhesion mediating protein, is injected into the port 2 and the inner bore of the microchannel 51 is coated with the protein. This is then stored to allow adherence of this ligand to the walls 53, 54 and 55 of the microchannel 51. In this embodiment, the microchannel was approximately 20 cm in length. A liquid sample carrying a specific cell in suspension was then injected into the port 2 and the subsequent progress of the cells was observed.

Figure 5:
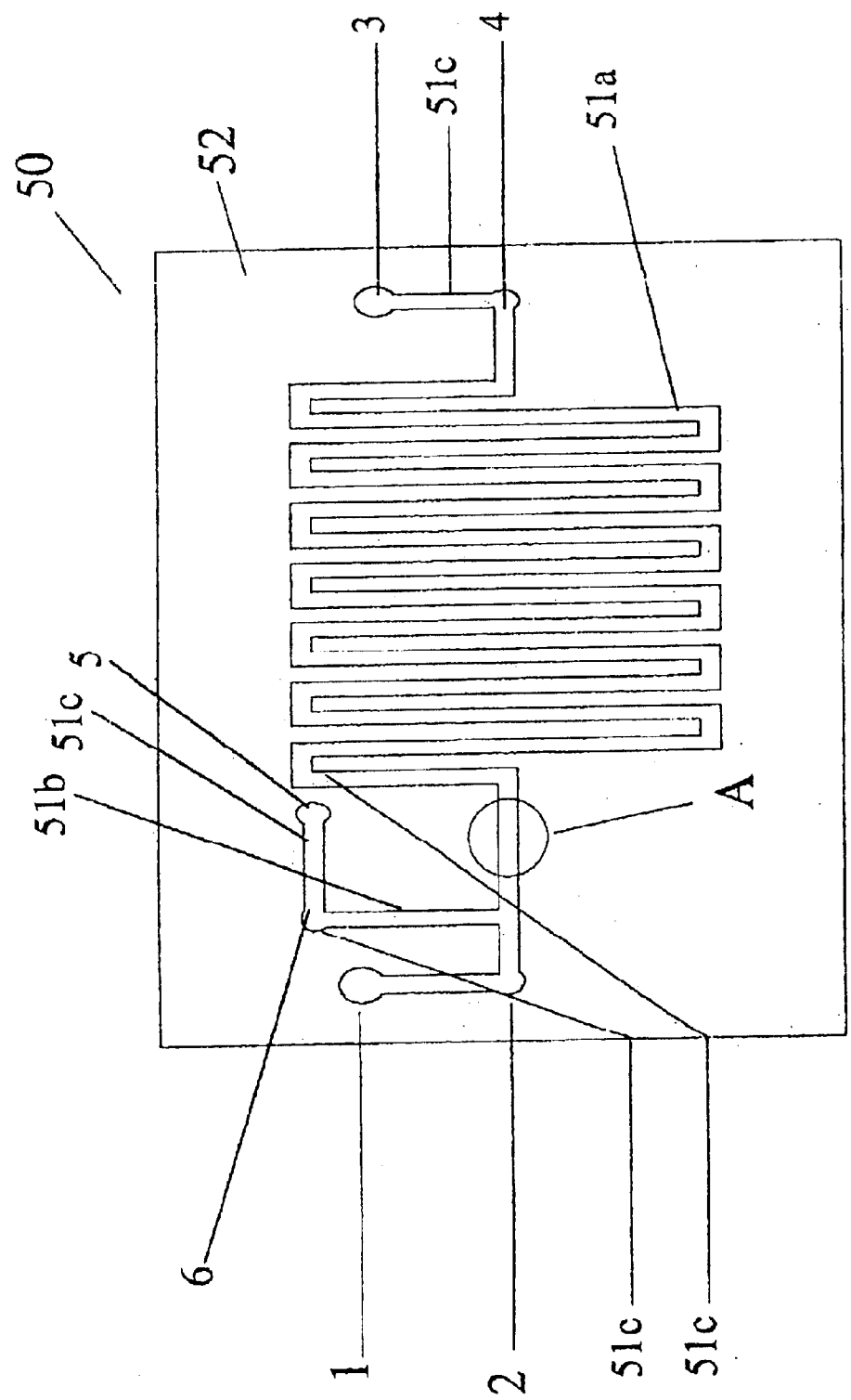
FIG. 5 is an enlarged view of the circled portion identified by the reference letter A in FIG. 1.

In the various embodiments, the cells are identified by the reference letter C and by suitable lowercase lettering in brackets. In FIG. 5, the arrow F gives the direction of flow of the liquid sample and numeral 75 identifies the ligand. Cells C(a) can be observed as flowing normally through the microchannel 51 while finally the cell C(c) is starting to adhere to the ligand 75. This is again circled and identified by the reference letter A and is shown in more detail in FIG. 6.

Figure 6:
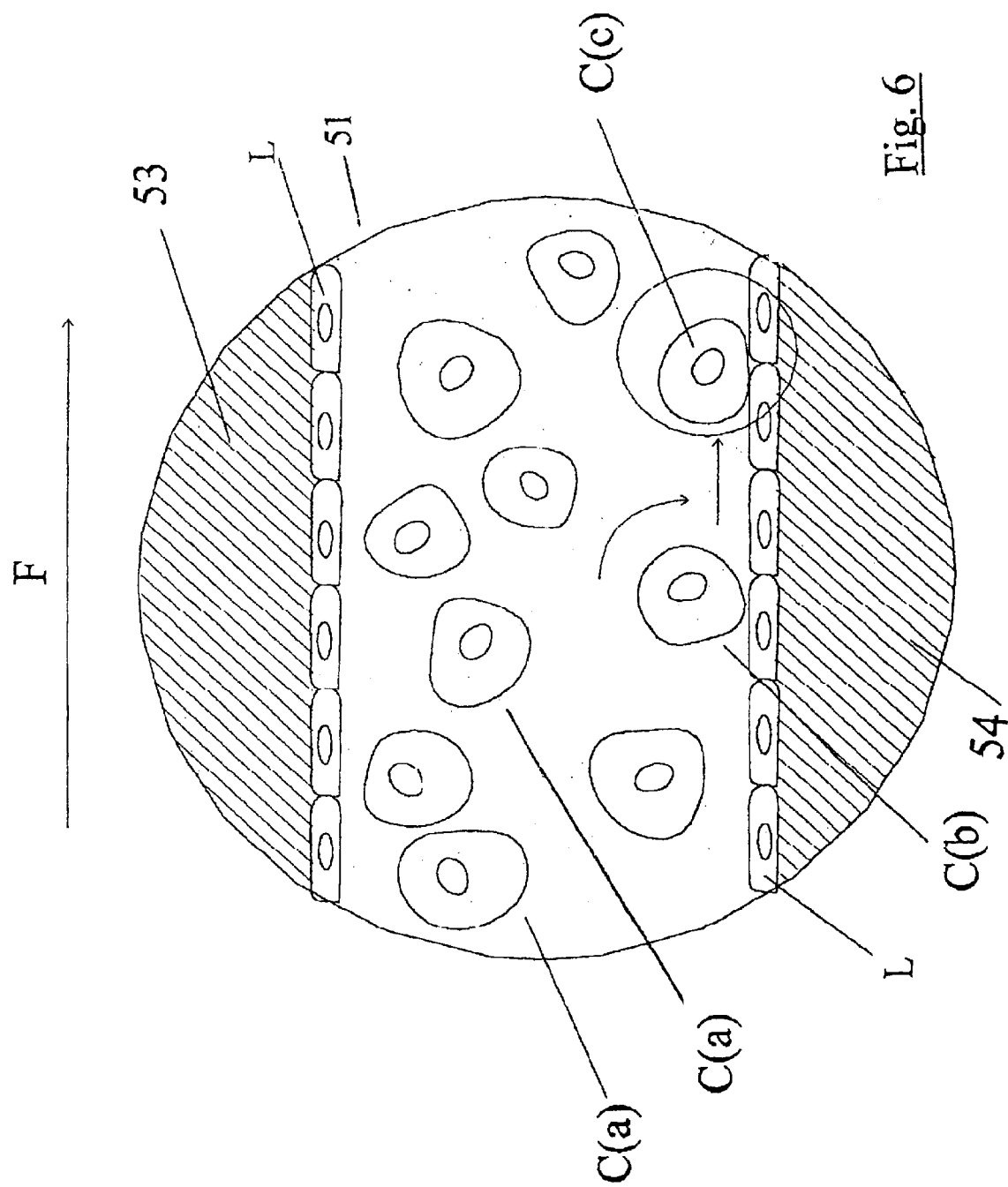
FIG. 6 is a further enlarged view of the circled portion identified by the reference letter A in FIG. 5.

Referring now to FIG. 6, the cell C(c) is shown just beginning to attach to the ligand 75. The cell C(d) is shown adhering strongly to the ligand 75, in this case, the protein, on the channel wall 54 with adhesion plaques, identified by the reference $C_1$. Finally, the cell C(e) is shown starting to migrate away from the ligand 75 with the leading edge of the cell $C_2$ starting to pull away from the ligand 75 with the leading tether $C_1$ starting also to elongate and break its contact with the ligand 75.

Figure 7:
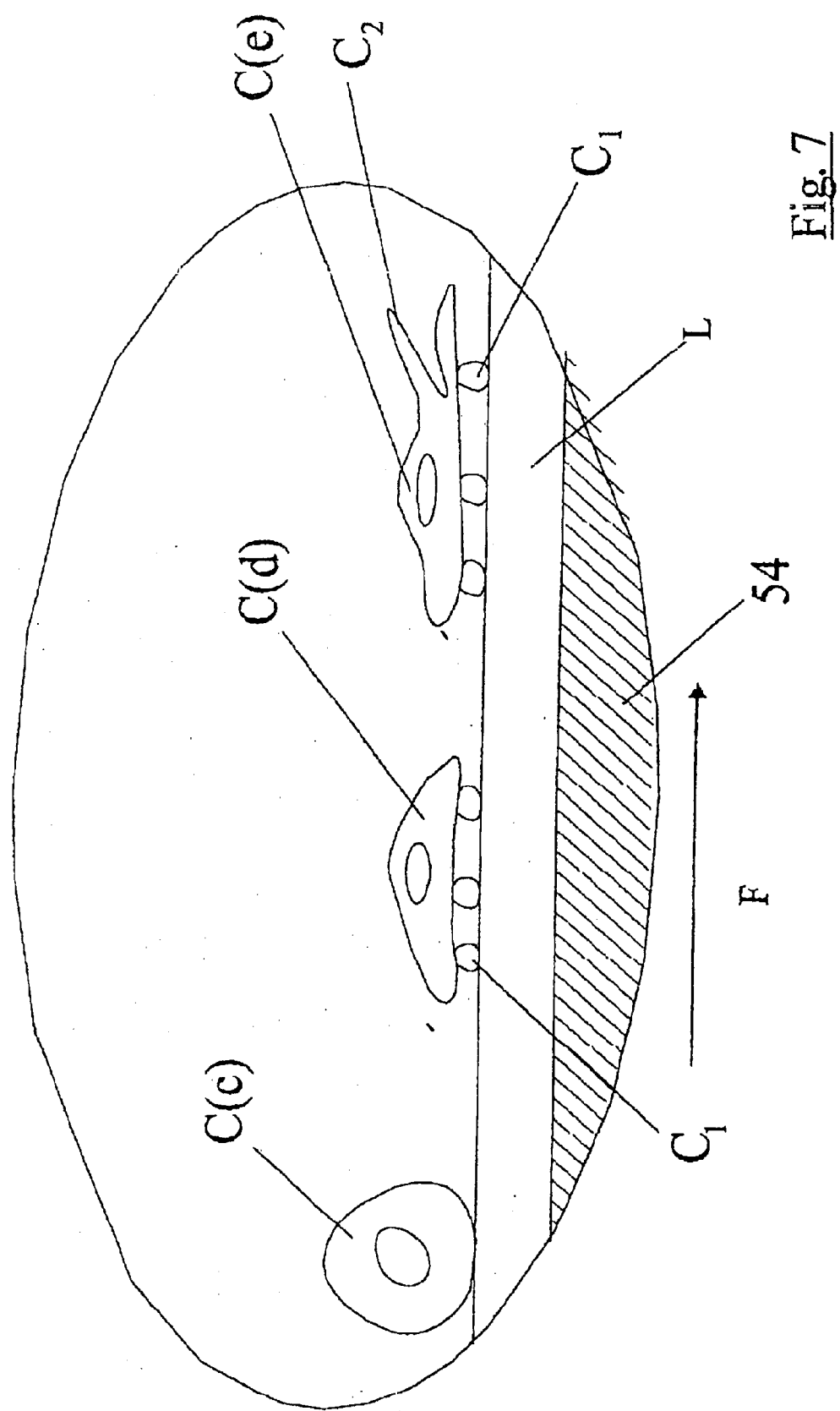
FIG. 7 is an enlarged portion of the biochip identified by the letter A in FIG. 1 for a different assay.
Figure 8:
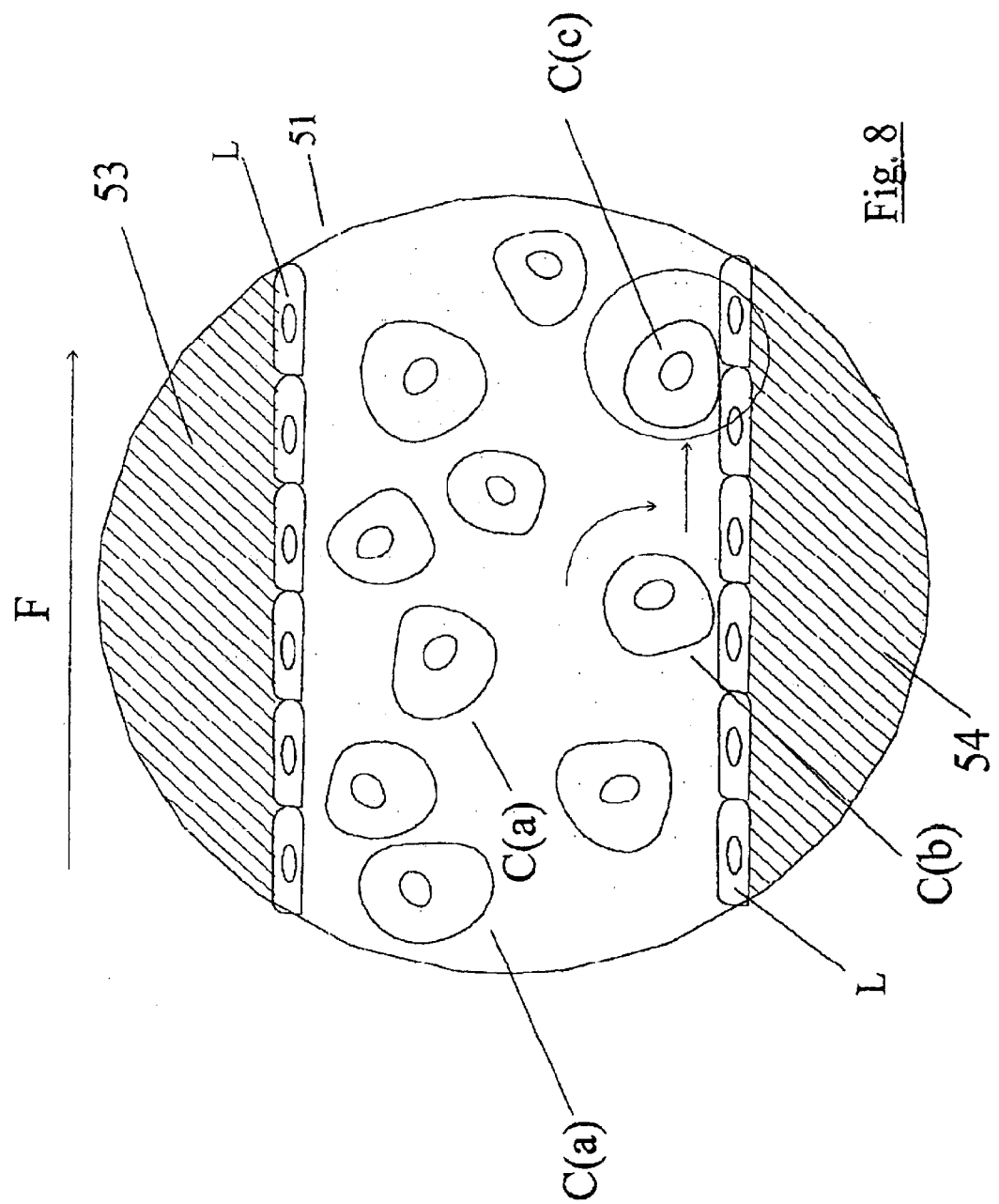
FIG. 8 is an enlarged view of the circled portion identified by the reference letter A in FIG. 7.

Referring now to FIGS. 7 and 8, in this assay, the ligand was provided by the seeding and subsequent growth of endothelial cells. This ligand is shown and identified by the reference numeral 76 in FIGS. 7 and 8 and the cells are identified by the same reference numerals. Strictly speaking, the ligands which are available to bind to the receptors on the cells C(c) are on the surface of the endothelium cells. Endothelial cells were chosen as a HUVEC cell line.

Referring now to FIG. 4, it will be seen that the biochip assembly 60 consists of six biochips 50, all of which can be used for the test previously described. It will be appreciated that, for example, many other tests can be carried out simultaneously. For example, the common port 26 can be used, for example, to coat all the biochips 50(a) to 50(f) with the one ligand or to inject the one sample liquid.

Therefore, variations of the test can be carried out such as, for example, assaying one cell type and several ECM ligands. Then each of the biochips 50 would be coated with a different adhesion mediating ligand. Using the same pumping system, you inject at port 2 with flow through the output port 4 for 50(a), you inject at port 6 and the output at port 8 for 50(b), and so on. Having coated all the microchannels with the chosen ECM ligands, the specified cell type is injected then through the common port 26. This allows the researcher to build up a profile of the characteristic behaviour of a cell type in response to particular ECM ligands. The same test can then be carried out using different cell types and one ECM ligand in which case the ECM ligand would be injected at port 26 with outputs at ports 2, 6, 10, 14, 18 and 22 followed by subsequent injection of different cell types into each of the biochips 50(a) to 50(f) injecting at port 4, 8, 12, 16, 20 and 24. This will allow the option of classifying an ECM ligand according to the behaviour of different cell types with regard to the multistep progress of rolling, tethering, adhesion and subsequent migration. Similarly, this can be done for several cell types with the one endothelial layer.

Still dealing with the apparatus and the biochips of FIGS. 1 and 4, it is possible to carry out a cell binding assay to identify proteins which will cause specific adherences of particular cell types. From the known initial concentration of cells passed through the biochip during the course of the assay, it is possible to obtain an accurate statistical and qualitative result regarding the percentage of cells which adhered to the coated walls, providing a clear quantitative result for the adhesion affinity of a specific ECM ligand. Here the adhesion affinity refers to the response of cell by adhesion to the ECM ligand-coated channel; i.e. the greater the number of cells adhered to a particular ECM ligand, the greater the adhesion affinity of that ligand. In addition, knowing the velocity of cells within the channels and the length of the channels themselves, it is also possible to obtain a clear physical result regarding the response time of the cell type to its environment. Thus, it is possible to calculate how long it takes the cell to react to its surroundings based on its site of adhesion within the microchannel structure, for example, a cell type has attached to the chosen ECM ligand or ligands, coating the microchannel walls image acquisition and recognition software may be employed to execute an automated based image acquisition or recognition of the cell type or indeed carry out any form of manual cell count.

Thus, for example, it is possible to do any of the following tests:

One cell type and one ECM ligand
One cell type and endothelium layer ligand
One cell type and several ECM ligands
Several cell types and one ECM ligand
Several cell types and endothelium layer ligand Obviously, various other variations, for example, various cell types and many ligands may also be used. The permutations and combinations are endless.

Finally, the binding affinity can be calculated from the shear stress required to cause dissociation of bound cells. By increasing the flow of velocity in the microchannel until there is dissociation of cells from the walls, it is possible to get a measure of the relative binding strengths of various ligands. Therefore, from the strength of the shear stress or corresponding velocity causing dissociation, this can be related to the binding affinity which a particular cell type has for a corresponding adhesion-inducing and mediating ligand. Needless to say, this could be applied to all the assays that have been carried out already. Any flushing liquid may be used, even the sample liquid itself.

Figure 9:
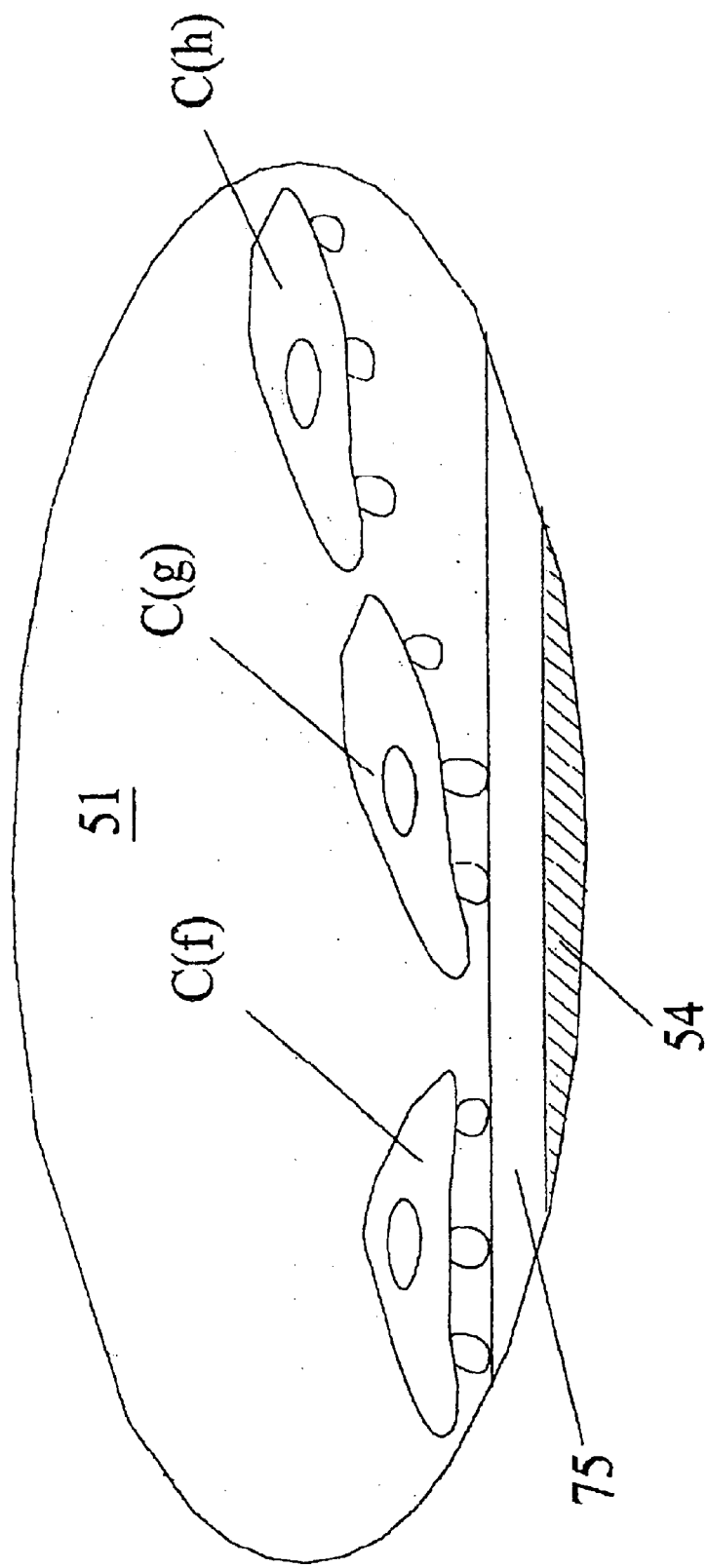
FIG. 9 is a view similar to FIG. 8 showing a different assay according to the invention.

Referring now to FIG. 9, there is illustrated a view similar to FIG. 7 in which parts similar to those described with reference to the previous drawings are identified by the same reference numerals. In this assay, following adhesion of the cell type to the corresponding adhesion-inducing and mediating ECM ligand, an adhesion inhibiting reagent, recombinant or cell derived, is injected at port 2 with an output at port 4, of the biochip 50 of FIG. 1. The cell C(f) can be seen securely anchored to the ligand 75, 10 then as C(g) beginning to separate and finally at C(h) having separated totally from the ligand. After the dissociation of the cell type from the chosen ECM ligand coating the microchannel wails, it is possible to use image acquisition/recognition software to do an automated based, image acquisition/recognition of cell type or manual cell count to calculate how many cells have responded by clear dissociation from the adhesion-inducing/mediating ECM ligand(s), again providing a clear result for the dissociation affinity of a specific reagent. Here the dissociation affinity refers to the response of a cell by dissociation from the ECM ligand-coated channel; i.e. the greater the number of cells dissociated from the particular ECM ligand, the greater the dissociation affinity of that reagent. Since the percentage of cells from the initial sample of known cell concentration is known, the dissociation affinity results in determination of the percentage of the adhered cells which subsequently dissociated. An identical test can be done for an endothelium layer and one detachment reagent. Then, using the assay assembly 60, many variations on the test can be carried out which will be easily apparent, whether they be one cell type and several ECM ligands and one or more detachment reagents; one ECM ligand, several cell types and one or more detachment reagents; several cell types, one endothelium layer and one or more detachment reagents. Obviously, all these variations will be readily apparent once it is appreciated that the assay assembly 60 is available.

Figure 10:
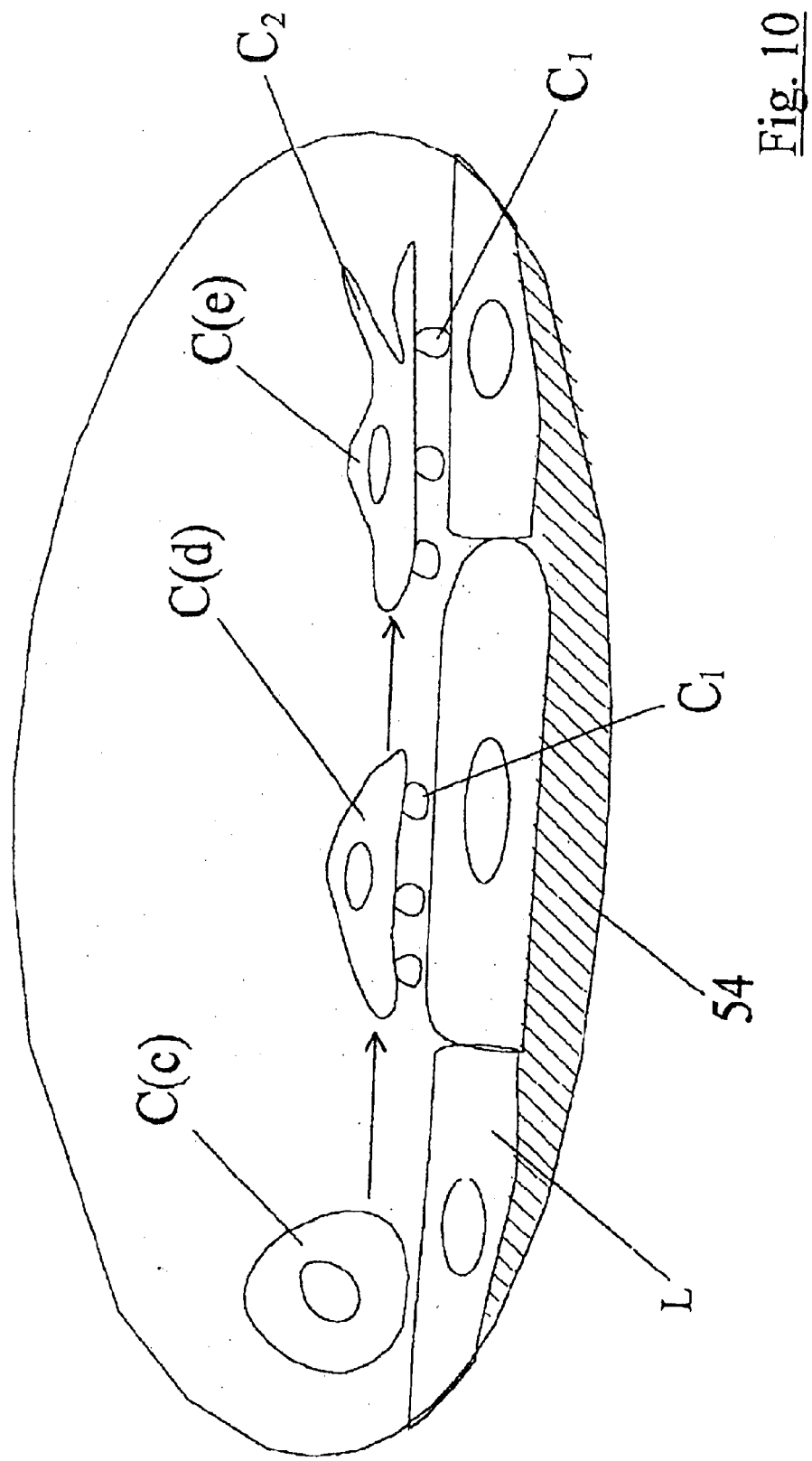
FIG. 10 is a plan view similar to FIG. 1 of an alternative construction of biochip.

Referring to FIG. 10, there is illustrated a modified form of the biochip illustrated in FIG. 1 and since it is substantially identical to the biochip in FIG. 1 it is identified by the same reference numeral 50 and similar parts are identified by the same reference numerals. In this embodiment, there is an additional input port 3 with an associated bubble-release port 4.

Figure 11:
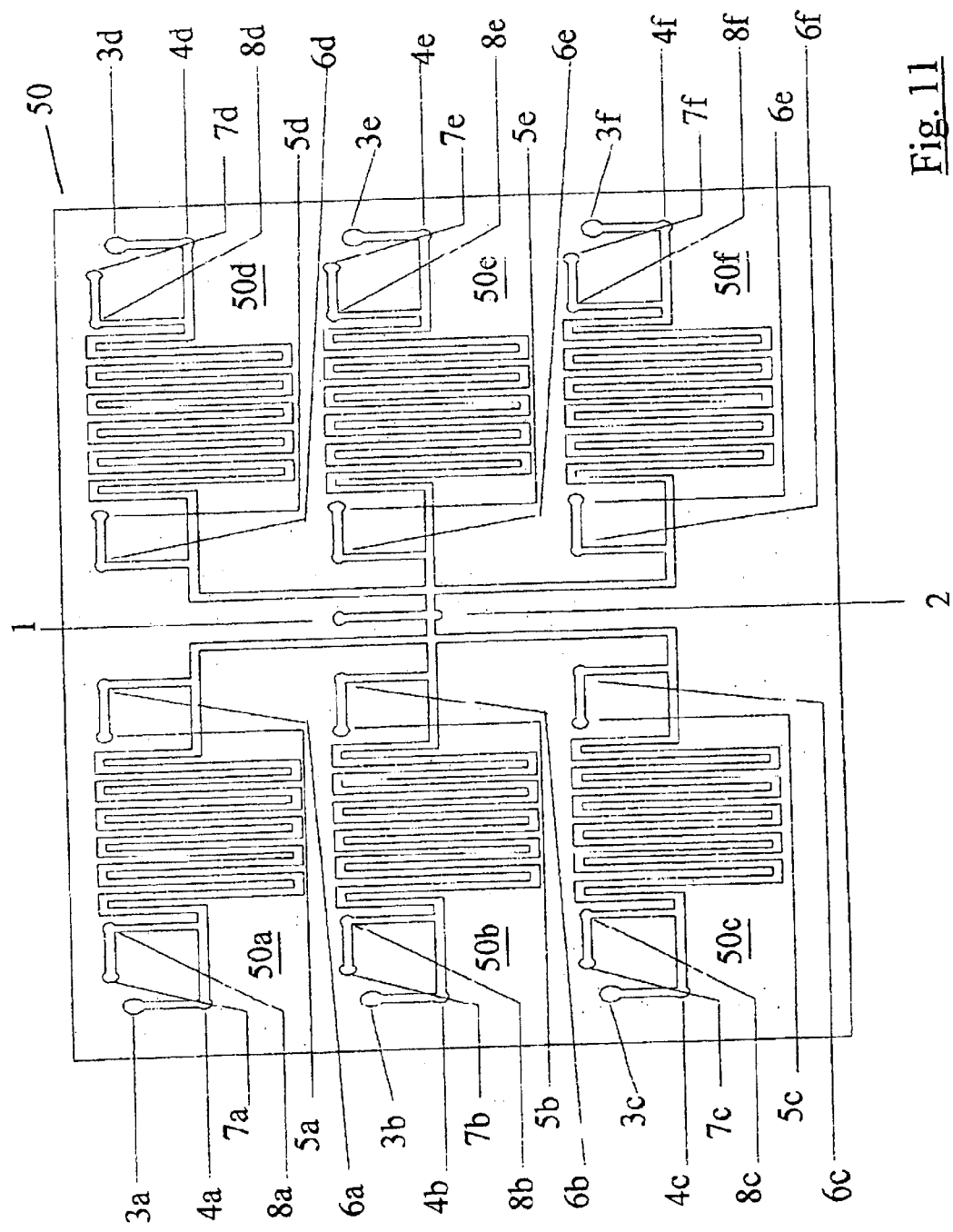
FIG. 11 is a plan view of a biochip assembly utilising the biochips of FIG. 10.

FIG. 11 illustrates another biochip assembly, indicated again by the reference numeral 60 incorporating the biochips 50(a) to 50(f) of FIG. 10.

The construction of biochip and biochip assembly of FIGS. 10 and 11 is particularly useful for chemokine, cytokine and chemoattractant induced cellular arrest assays.

Figure 12:
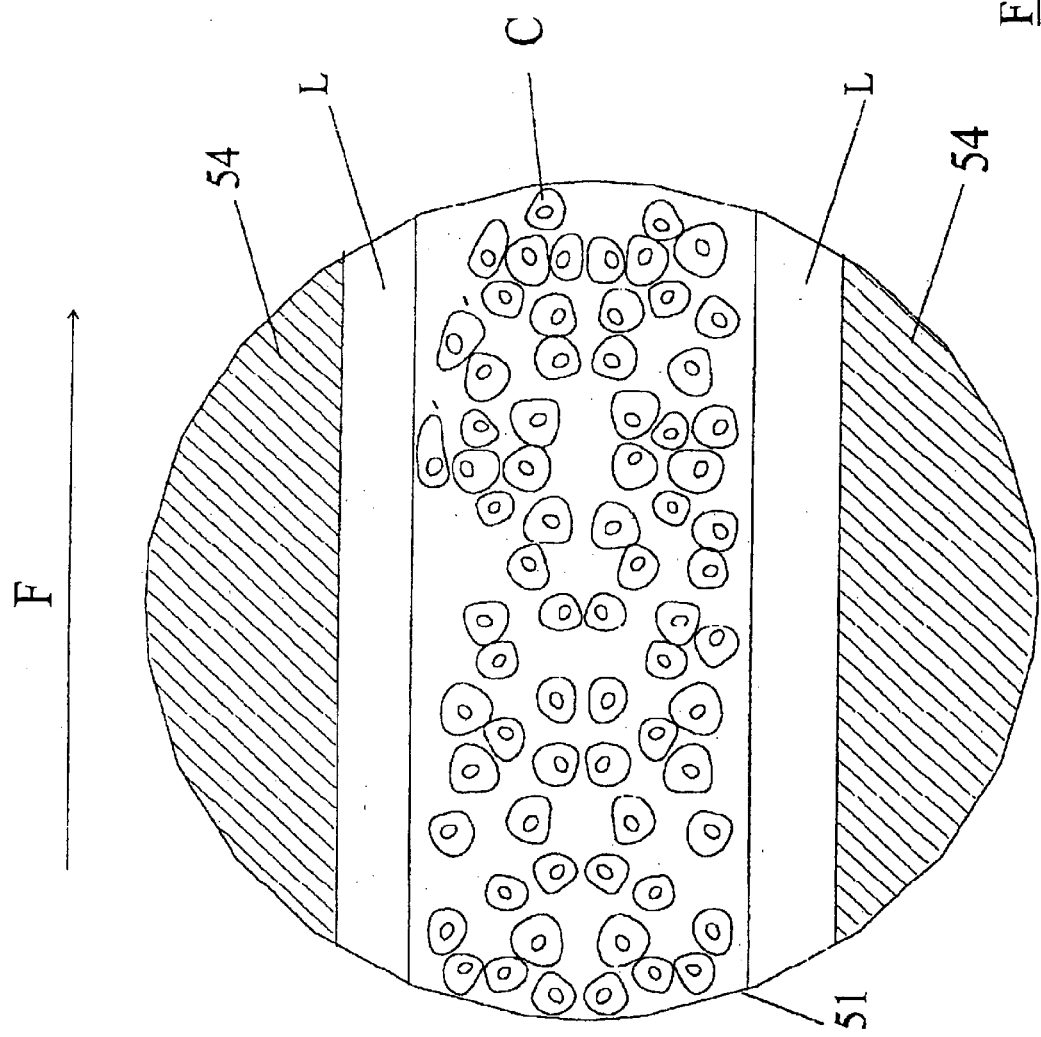
FIG. 12 is an enlarged view of the circled portion identified by the letter A in FIG. 11 illustrating one assay.

Referring now, for example, to FIG. 10, the biochip 50 can be used in assays is to determine whether a cell, for example, a lymphocyte crawling in response to a particular chemoattractant is integrated with the endothelial or ECM ligand utilised. Again, in this assay the walls of the microchannel are coated with a single adhesion-mediating/inducing ECM injected at port 2, and outputted at port 6. Once it is ready, then essentially the same assay as carried out before with a subsequent measurement of the crawling caused by the chemoattractant which is injected at port 4 with an output at port 6. FIG. 12 which is substantially similar to FIG. 5 illustrates this. Needless to say, instead of using an ECM ligand, an endothelium layer may also be used.

Then, to investigate cellular navigation, the biochip assembly of FIG. 11 may be used to determine whether a cell crawling in response to chemokine is integrated with the nature of the ECM ligand used. Thus, for example, one ECM protein may be injected at port 38 with outputs at ports 2, 4, 6 and 8 for biochip 50(a), 50(b) and so on. Then, a particular cell type can be injected at port 38 with output at port 2 for biochip 50(a), port 8 for biochip 50(b) and so on. A chemoattractant would then be injected in port 6 with output at port 2 for biochip 50(a) and then a second different chemoattractant would be injected at port 12 with an output at port 8 for the biochip 50(b) and so on. Additionally, the assay can be used using multiple cell types, one ECM ligand and several chemoattractants, and so on. In other words, there are many permutations and combinations to study cellular navigation.

Cellular activation can be studied using the biochip assembly 60 of FIG. 11. The purpose of the assay is to determine if the nature of the cell (e.g. lymphocyte) activation determines binding specificity or preference for either the ECM ligand or an individual chemoattractant migratory signals. In this case, the microchannels of each individual biochip 50(a) to 50(f) are individually coated with specific matrix ligands, e.g. fibronectin, collagen or hyaluronic acid in the case of lymphocytes injected at port 2 with output at port 6 for biochip 50(a), injected at port 8 and output at port 12 for biochip 50(b), and so on. Cells are permitted to crawl through a protein coated channel before encountering multiple channels coated with individual matrix molecules by injecting the protein at port 38, output at ports 6, 12, 18, 24, 30 and 36, injecting the cell type at port 38 with output at ports 2, 8, 14, 20, 26 and 32. The choice of channel can be analysed with response to the nature of the cell activation or nature of the chemoattractant signalling. In this case, one or several chemoattractants may be incorporated, for example, injecting the first chemoattractant at port 4 with output at port 6 for biochip 50(a), injecting the next chemoattractant at port 10, output at port 12 for biochip 50(b), and so on. Hence, cells will be activated utilising multiple individual signals. The effects of such activations can be studied to determine whether the nature of activation determines either ligand or chemoattractant preference.

It will be appreciated that these tests can be carried out using separate cell types, several ECM ligands and several chemoattractants. Again, the variations are endless. Indeed, one cell type, an endothelium layer and several chemoattractants may be assayed, as can several cell types, the one endothelium layer and several chemoattractants.

Figure 13:
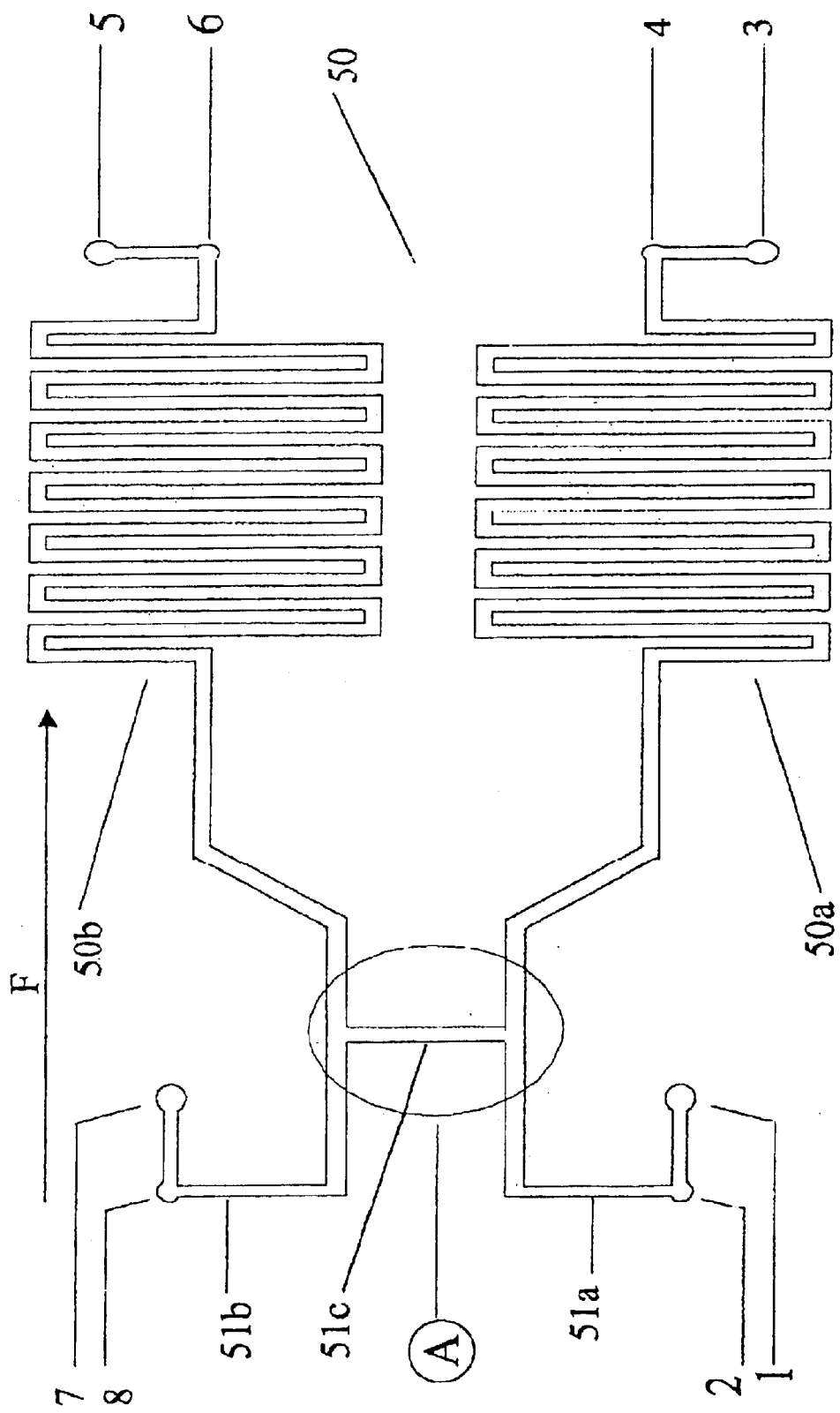
FIG. 13 is a plan view of another biochip according to the invention.
Figure 14:
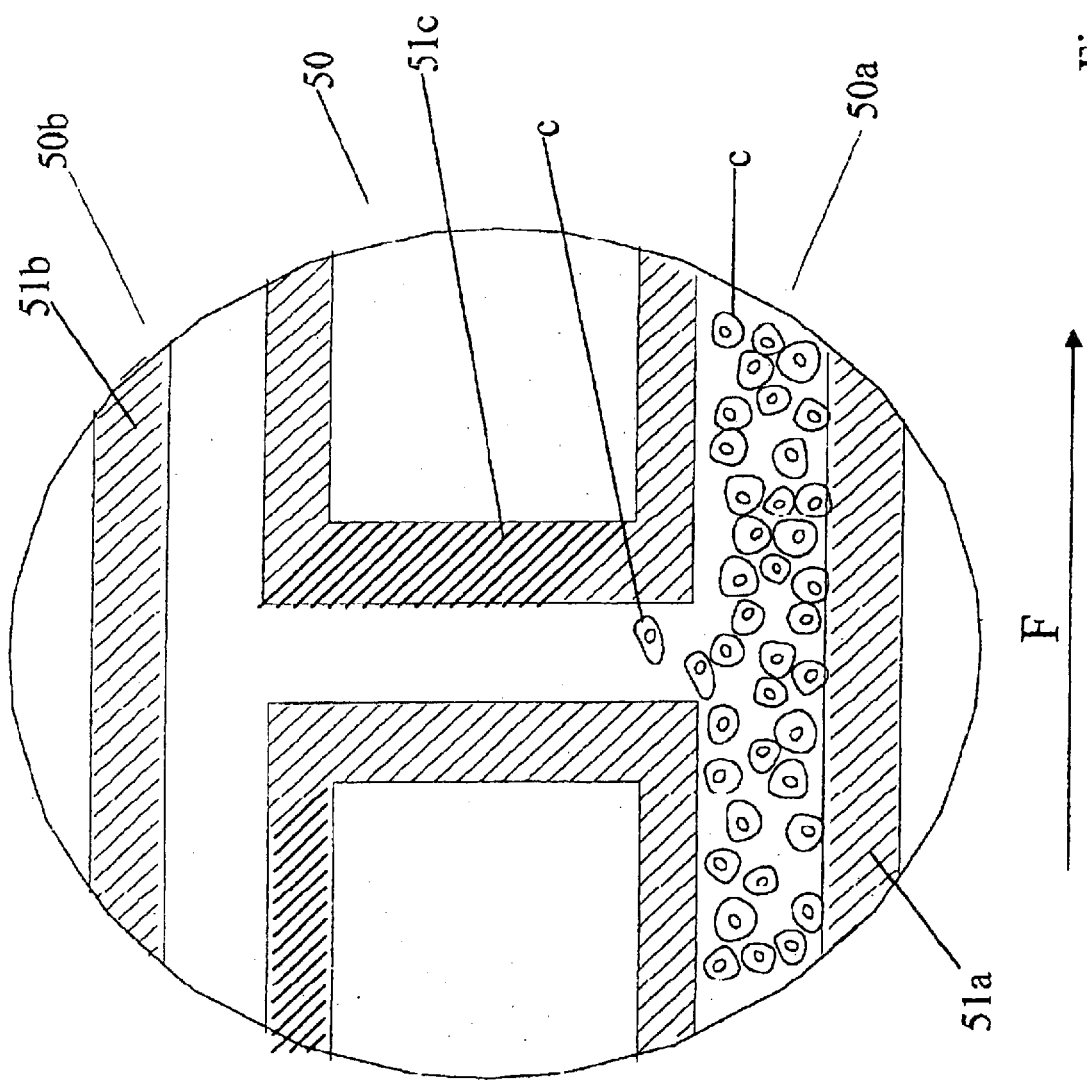
FIG. 14 is an enlarged view of the circled portion identified by the reference letter A in FIG. 13 illustrating another test.

Referring to FIGS. 13 and 14, there is illustrated an alternative construction of composite symmetrical biochip 50 in which there are two main microchannels, namely the microchannels biochip 51(a) and 51(b) having two main microchannels joined together by a connecting microchannel 51(c). In the microchannel 51(a), chemoattractant can be injected through the port 6 and the sample liquid through the port 8. Then, by judicious choice of the fluid flow of both the chemoattractant and the sample liquid, it is possible to introduce flow between the two channels, as illustrated in FIG. 14. Alternatively, it is possible to fabricate, effectively what is now a symmetrical biochip, in such a way that the pressure of the flow of the chemoattractant is equal to the pressure of the flow of the sample thereby resulting in no diffusion or leakage at the interconnecting channel with any movement of the cell through the connecting channel being caused by the chemoattractant.

FIGS. 15 and 16 and FIGS. 17 and 18 show still further alternative embodiments with views similar to FIGS. 13 and 14 respectively, except that in this case, it is the microchannel 51(a) which carries the sample.

Figure 19:
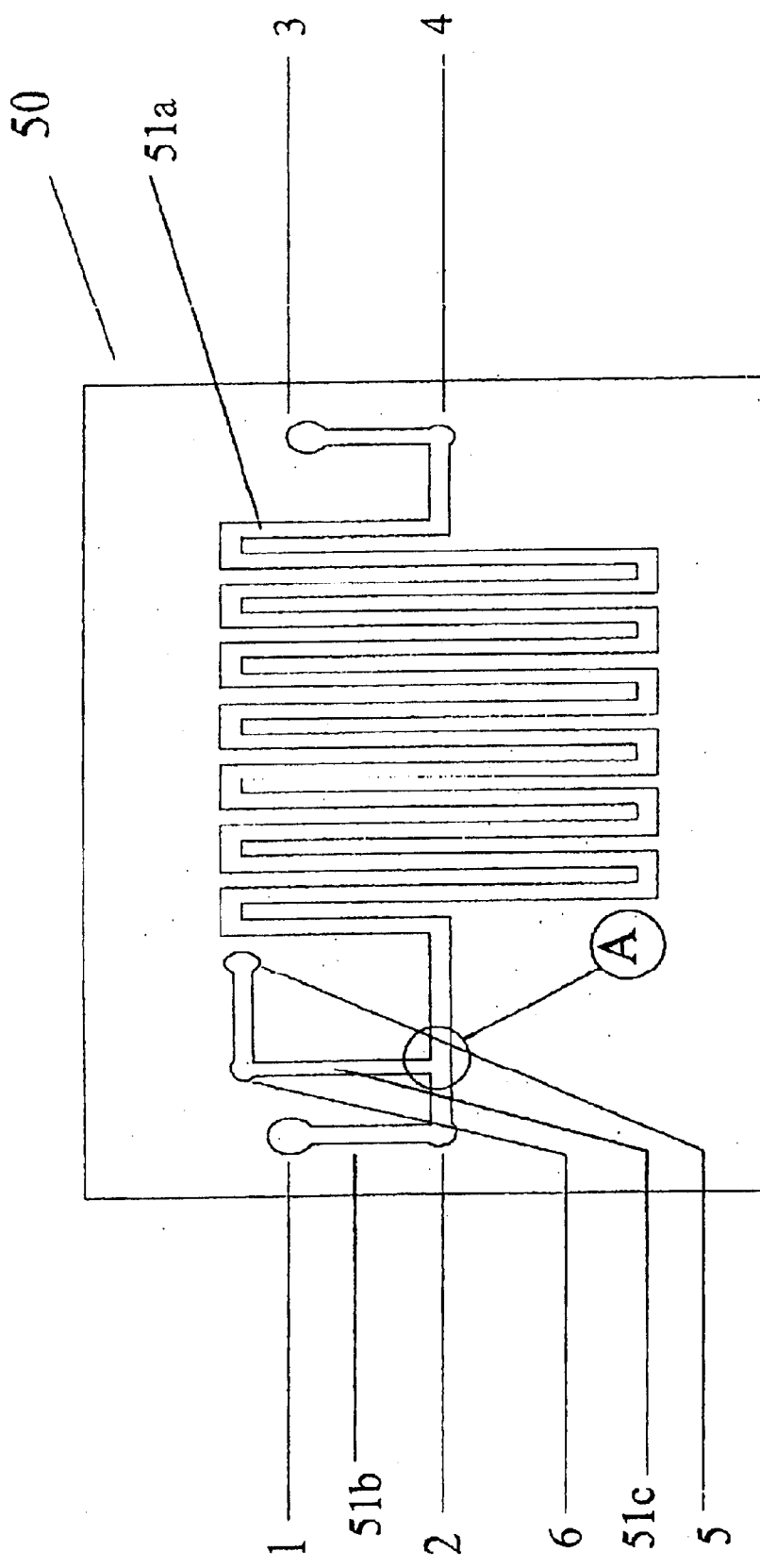
FIG. 19 is a plan view of a still further biochip according to the invention.
Figure 20:
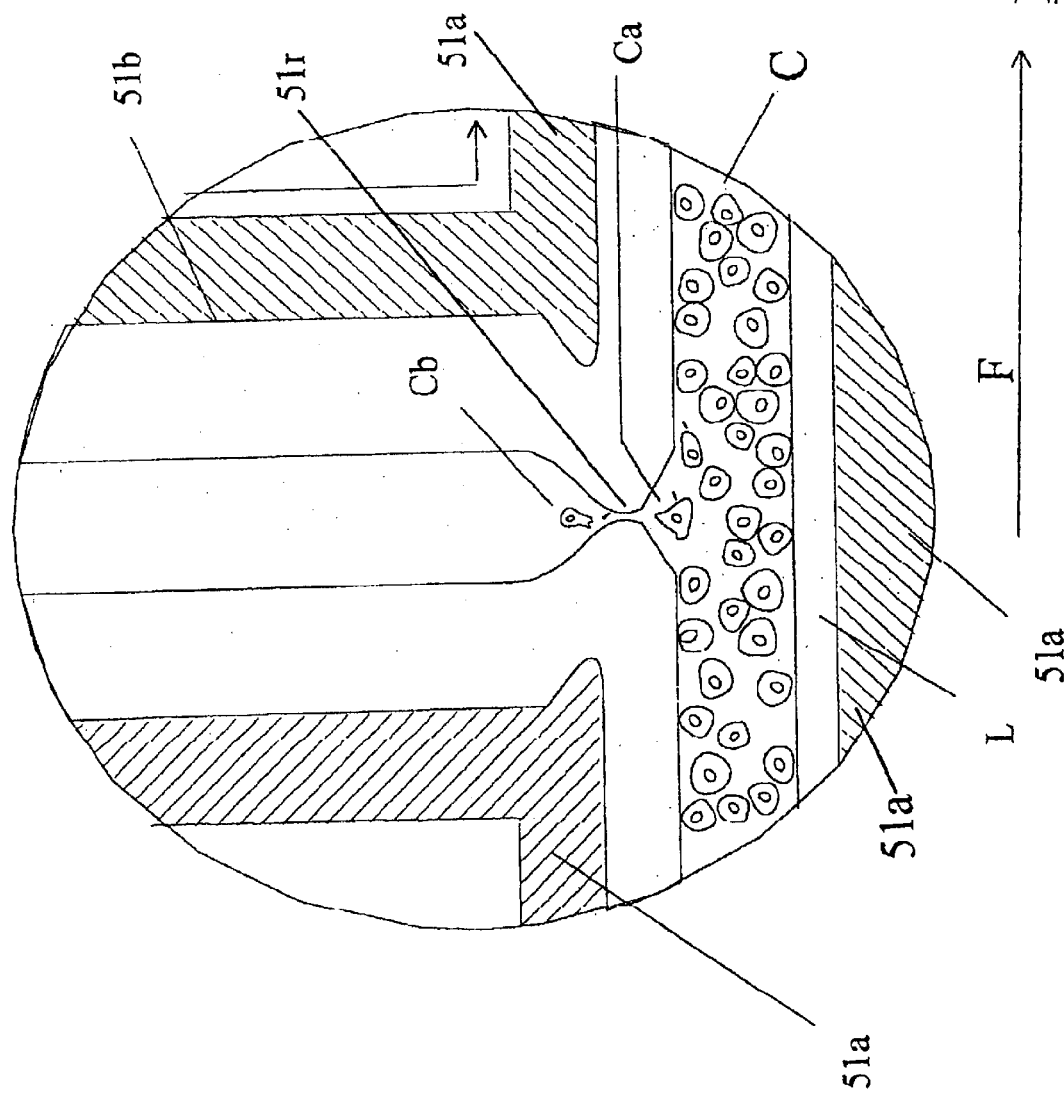
FIG. 20 is an enlarged view of the portion identified by the reference letter A in FIG. 19.

Referring to FIGS. 19 and 20, there is illustrated an alternative construction of biochip, again indicated generally by the reference numeral 50. In this embodiment, there is provided an additional inlet port 4 as heretofore, however, in this embodiment, the connection between the inlet port 4 and the main microchannel 51(a) is through a feeder microchannel 51(a) a restricted throat, as shown in FIG. 20. Essentially, this is for the injection of a chemoattractant such that the entrance diameter, that is to say, the cross-sectional area of the throat is smaller than the cross-sectional area of the cell C under examination when the cell C is in free suspension and flowing as illustrated in FIG. 20. Thus, for example, a cell $C_2$, on approaching the throat 56, has to squeeze itself through as illustrated by the cell $C_3$. FIGS. 19 and 20 show one cell type, one ECM ligand and one chemoattractant. Needless to say, using the same arrangement of biochip assembly 60, as illustrated in FIG. 11, with the restricted throat 56, multiple assays may be carried out. Accordingly, for example, assays with one cell type, one ECM ligand and one chemoattractant, or with one cell type, one endothelium layer and one chemoattractant, may be carried out with one biochip 50. However, for one cell type, one ECM ligand and several chemoattractants or several cell types, one ECM ligand and several chemoattractants, or one cell type, several ECM ligands, several chemoattractants, or several cell types, several ECM ligands and several chemoattractants, or one cell type, one endothelium layer and several chemoattractants, or indeed, several cell types, endothelium layer and several chemoattractants may all be assayed with the biochip assembly 60.

Figure 15:
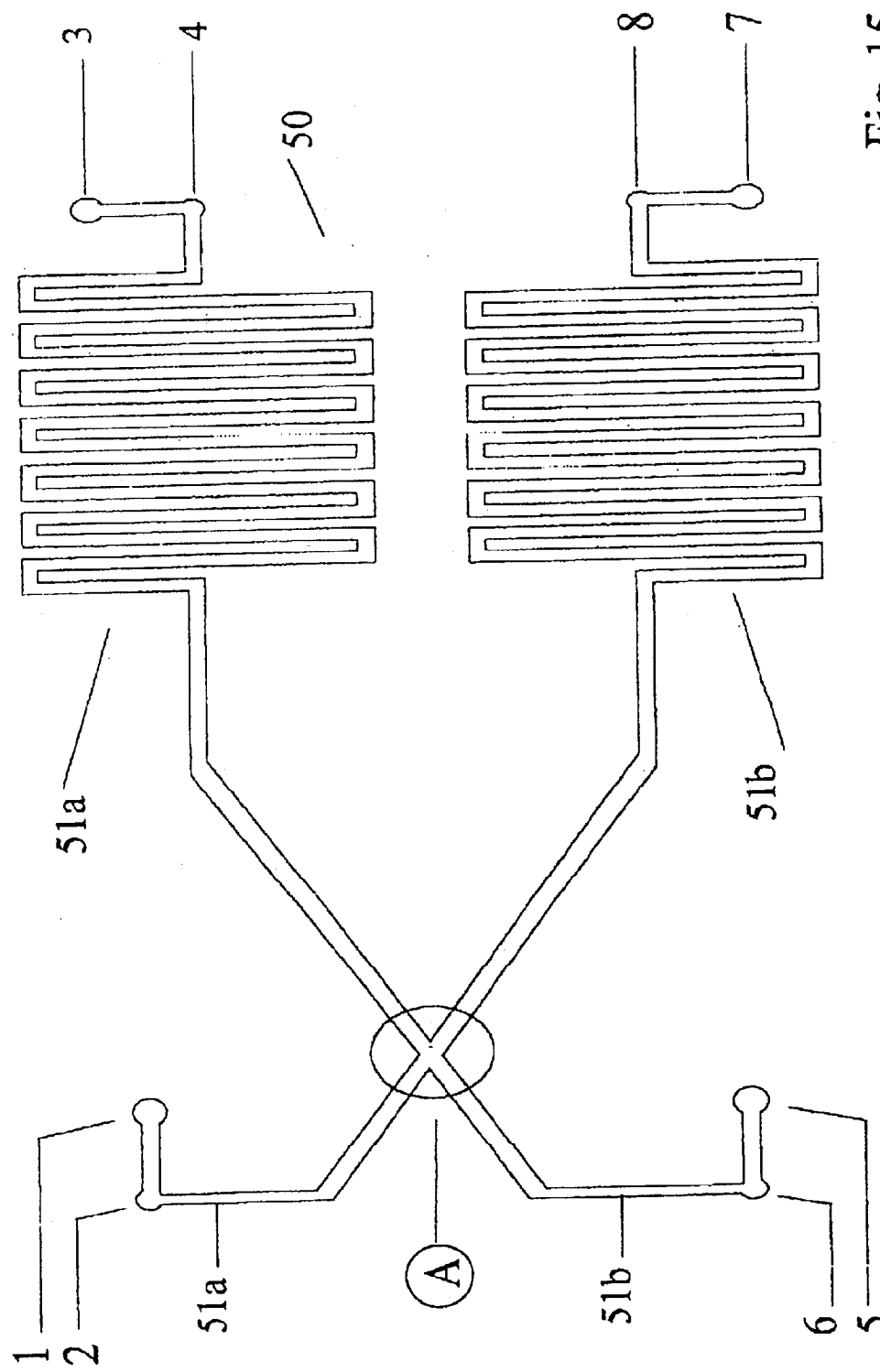
FIG. 15 is a plan view of a still further biochip according to the invention.
Figure 16:
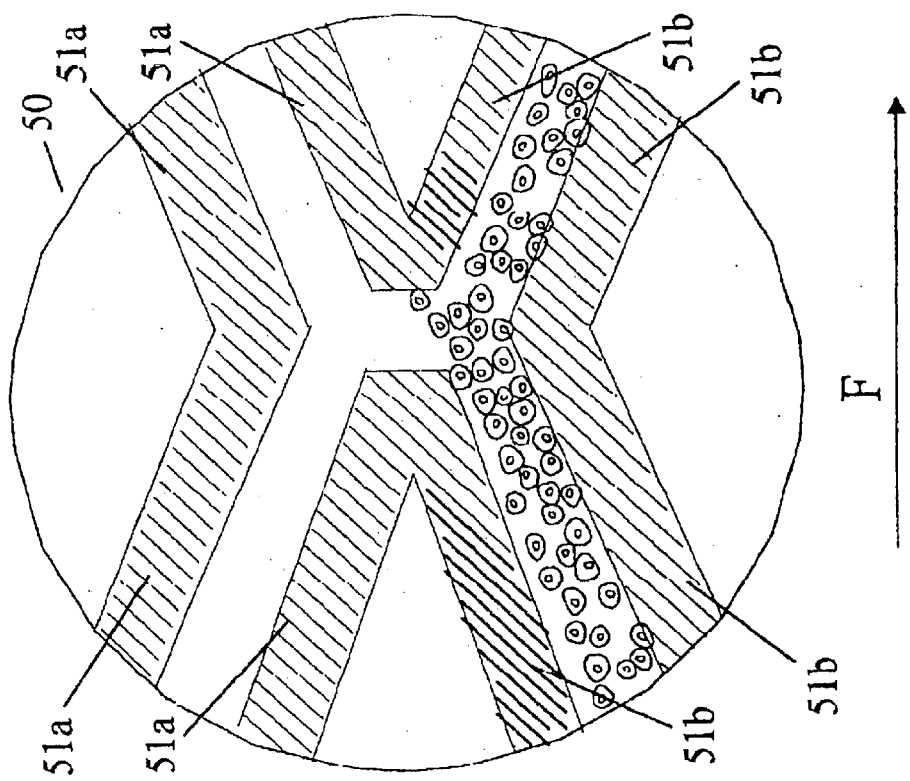
FIG. 16 is an enlarged view of the portion identified by the letter A in FIG. 15.
Figure 17:
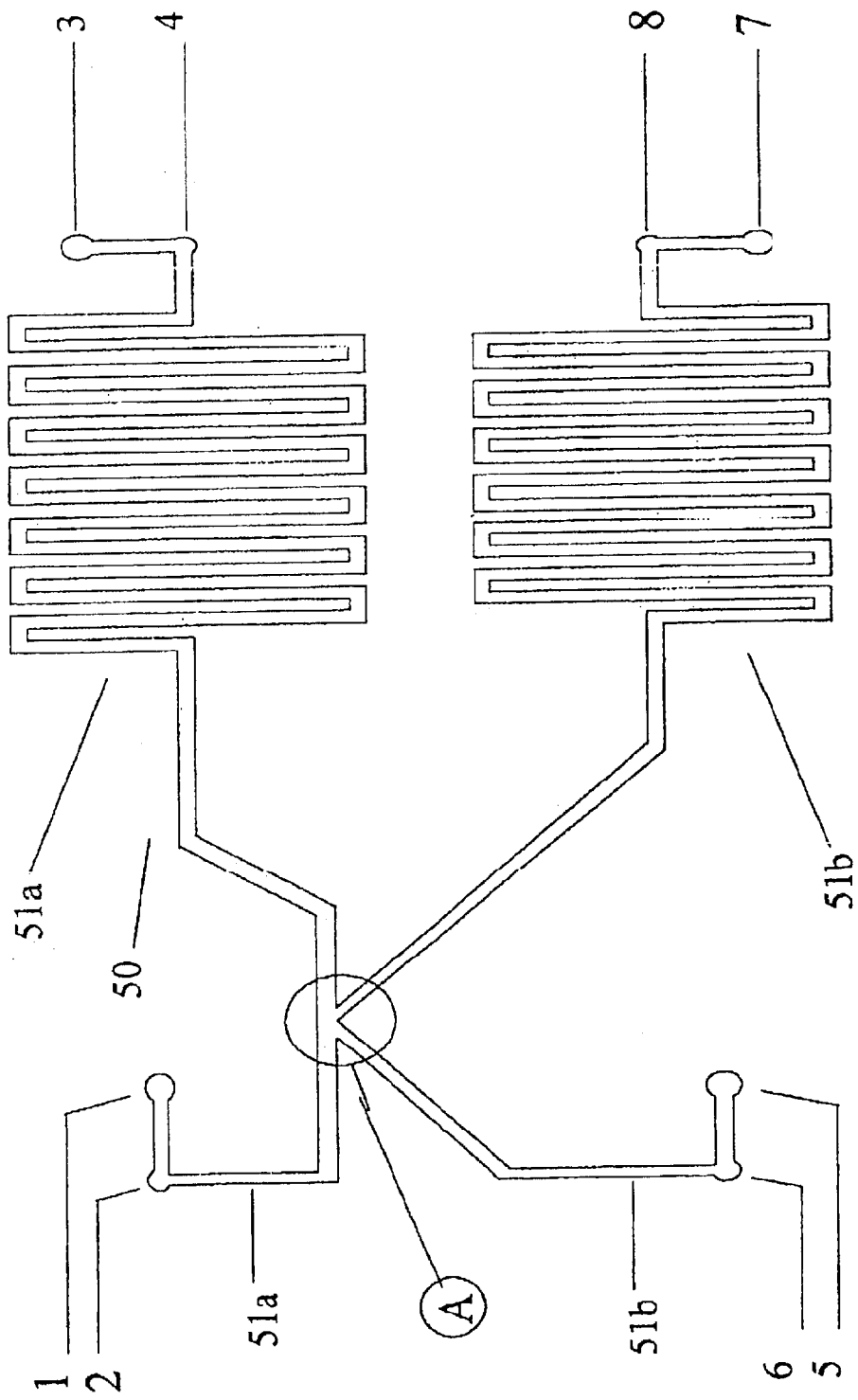
FIG. 17 is a plan view of a still further biochip according to the invention.
Figure 18:
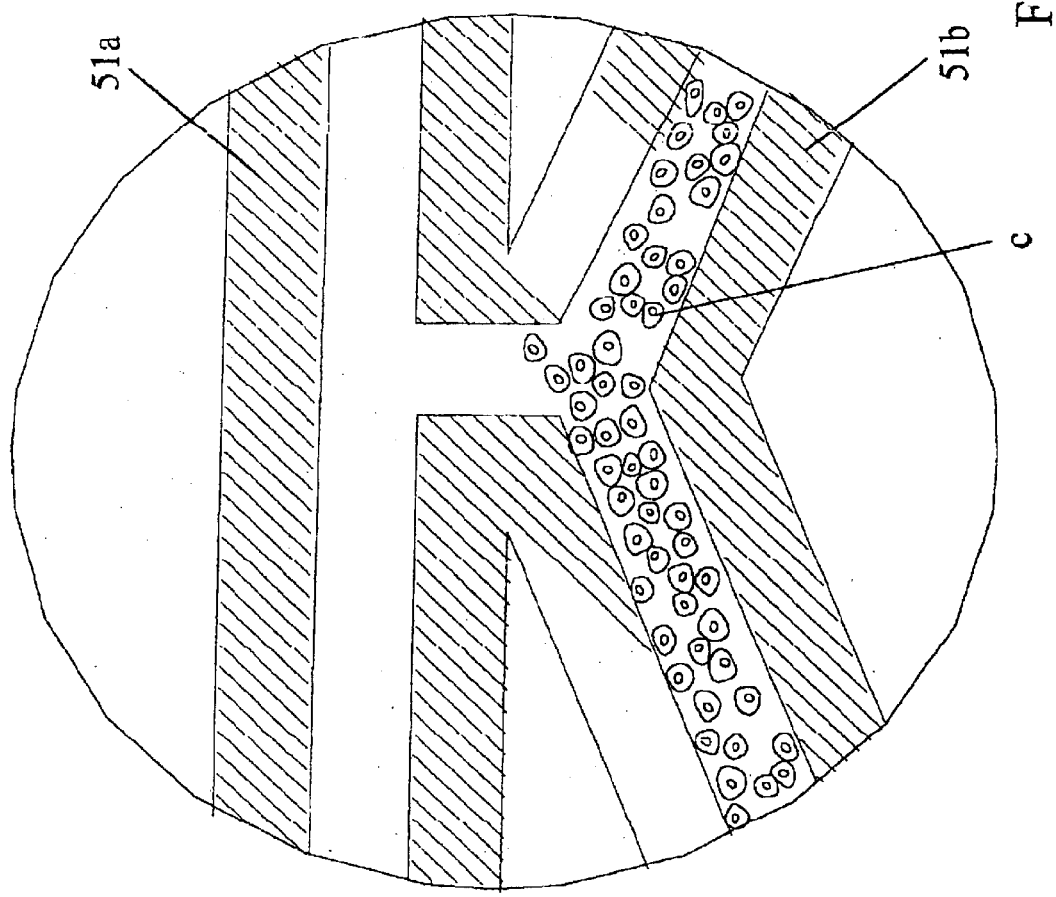
FIG. 18 is an enlarged view of the portion identified by the reference letter A in FIG. 17.

Similarly, the same arrangements of FIGS. 13 and 14; FIGS. 15 and 16; and FIGS. 17 and 18 could all be used subject to a restricted throat being provided. Needless to say, all of these embodiments may be altered in order to encompass several interconnecting sections enabling the execution of several separate tests in parallel.

Figure 21:
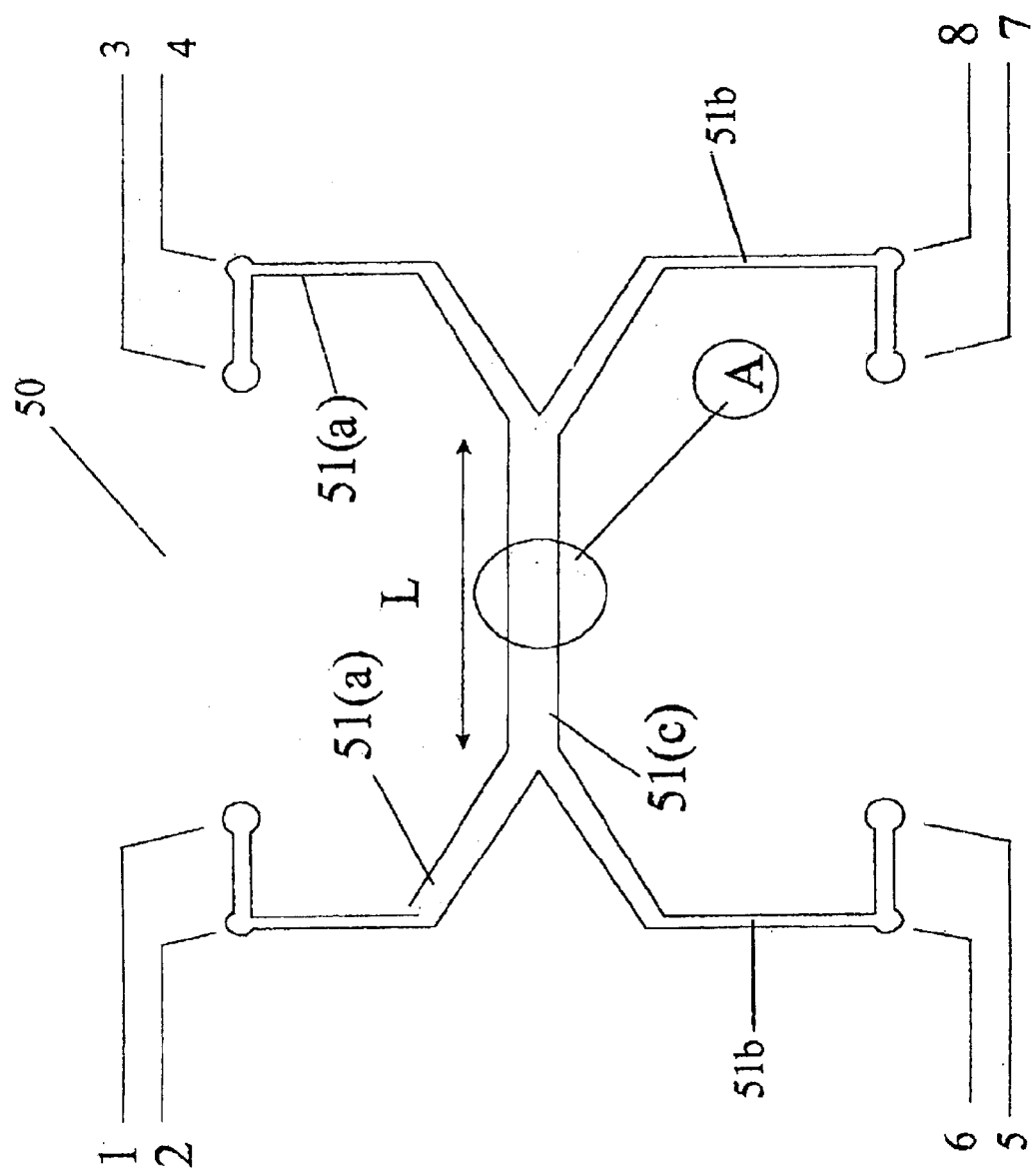
FIG. 21 is a plan view of a still further biochip according to the invention.
Figure 22:
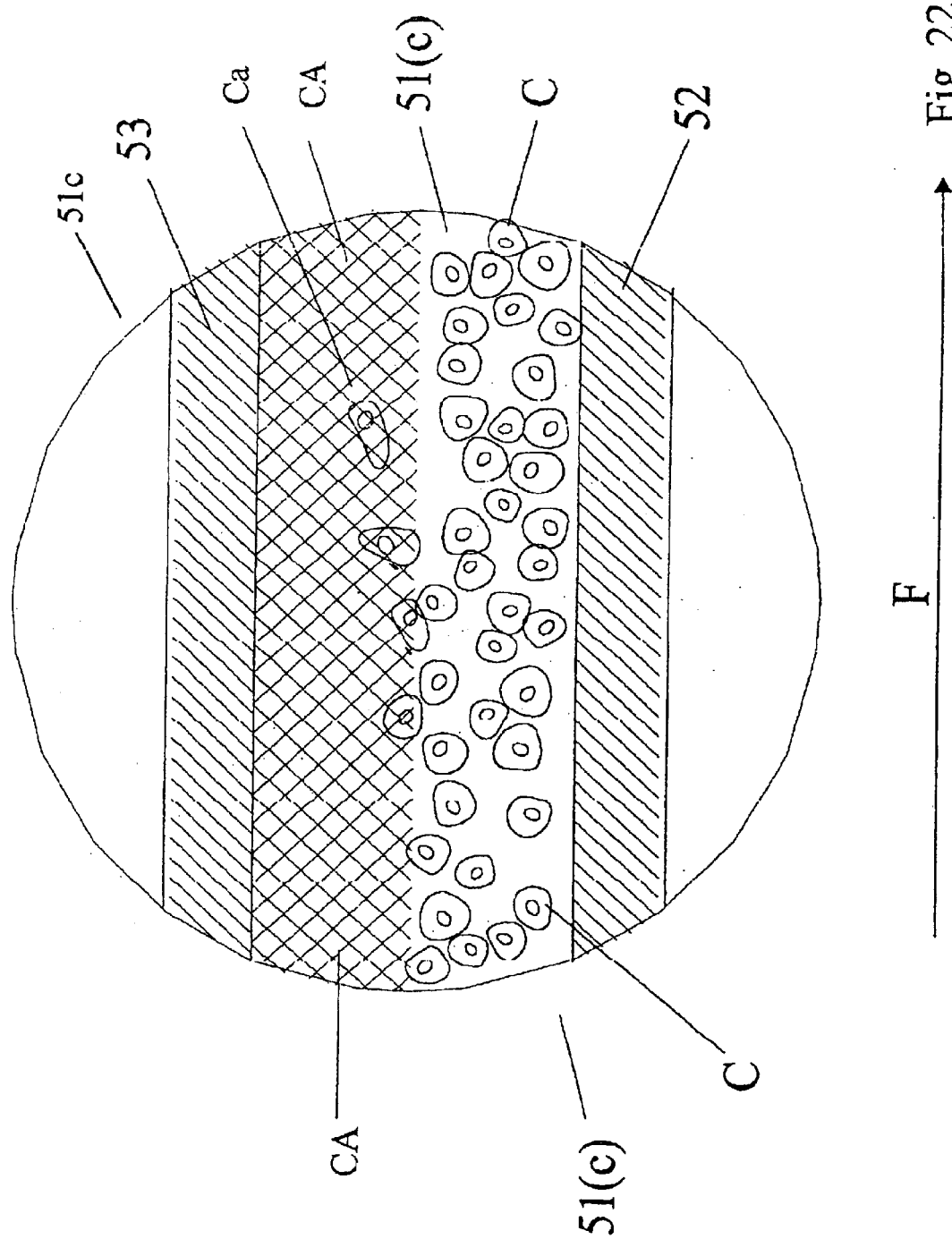
FIG. 22 is an enlarged view of the circled portion identified by the reference letter A in FIG. 21.

Referring to FIGS. 21 and 22, there is provided a biochip again indicated generally by the reference numeral 50, comprising two separate main microchannels 51(*a*) and 51(*b*) connected by a connecting microchannel 51(*c*). One of the main microchannels 51(*a*) has input ports 2 and 4 and the other main microchannel 51(*b*) has outlet ports 6 and 8. All these ports have associated bubble-release ports 1, 3, 5 and 7 respectively. Parts similar to those described with reference to the previous drawings are identified by the same reference numerals. When it is desired to assay chemotaxis, namely, active swimming, towards chemoattractants, whether such chemoattractants are recombinant or cell-derived, the inlet port 2 has a chemoattractant delivered therethrough and the inlet port 4 has the sample liquid. These are identified as two streams, the chemoattractant 81 and the liquid sample again carrying cell C in suspension. FIG. 22 shows that as the liquid sample progresses, some of the cells, identified by $C_5$, progress into the chemoattractant 81. The microchannel therefore has multi-laminar flow of the chemoattractant 81 and the liquid sample carrying the cells C. If the channel length L is shorter than the diffusion of the chemoattractant or culture medium, then the assay will determine whether a cell's receptors may be activated prior to adhesion to a substrate.

Ideally, the microchannels of the biochip 50 are coated with a liquid silicone to provide a hydrophobic surface and thus the cells will not adhere to the microchannel walls so that any movement towards the chemoattractant will be solely due to active swimming and not to adhesions followed by subsequent migration.

Figure 23:
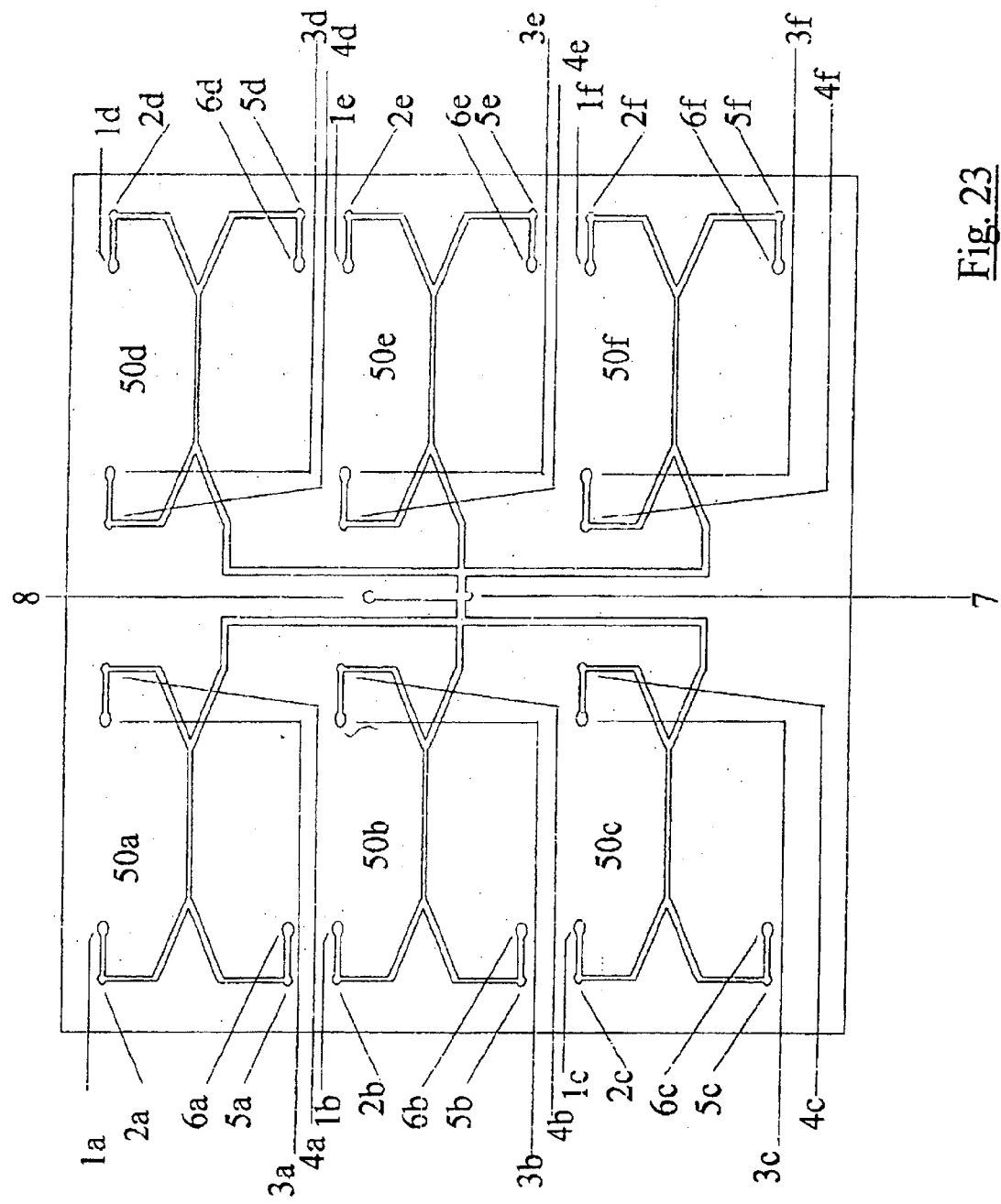
FIG. 23 is a plan view of a biochip assembly incorporating the biochip of FIG. 21.

Referring now to FIG. 23, there is illustrated a biochip assembly, indicated generally by the reference numeral 70, incorporating the biochips 50 of FIG. 21, identified again by the reference numeral 50 and the letters (a) to (f). In this particular biochip assembly 70, there is a common port 37 which connects to all of the interconnecting channels and thus several cell types and one chemoattractant may be tested or several chemoattractant and the one cell. For example, the apparatus of FIG. 23 could be used to filter out one cell type for collection from the other. Therefore, they could be in the form of a cell filtering or separation of one or more cell types from samples.

Figure 24:
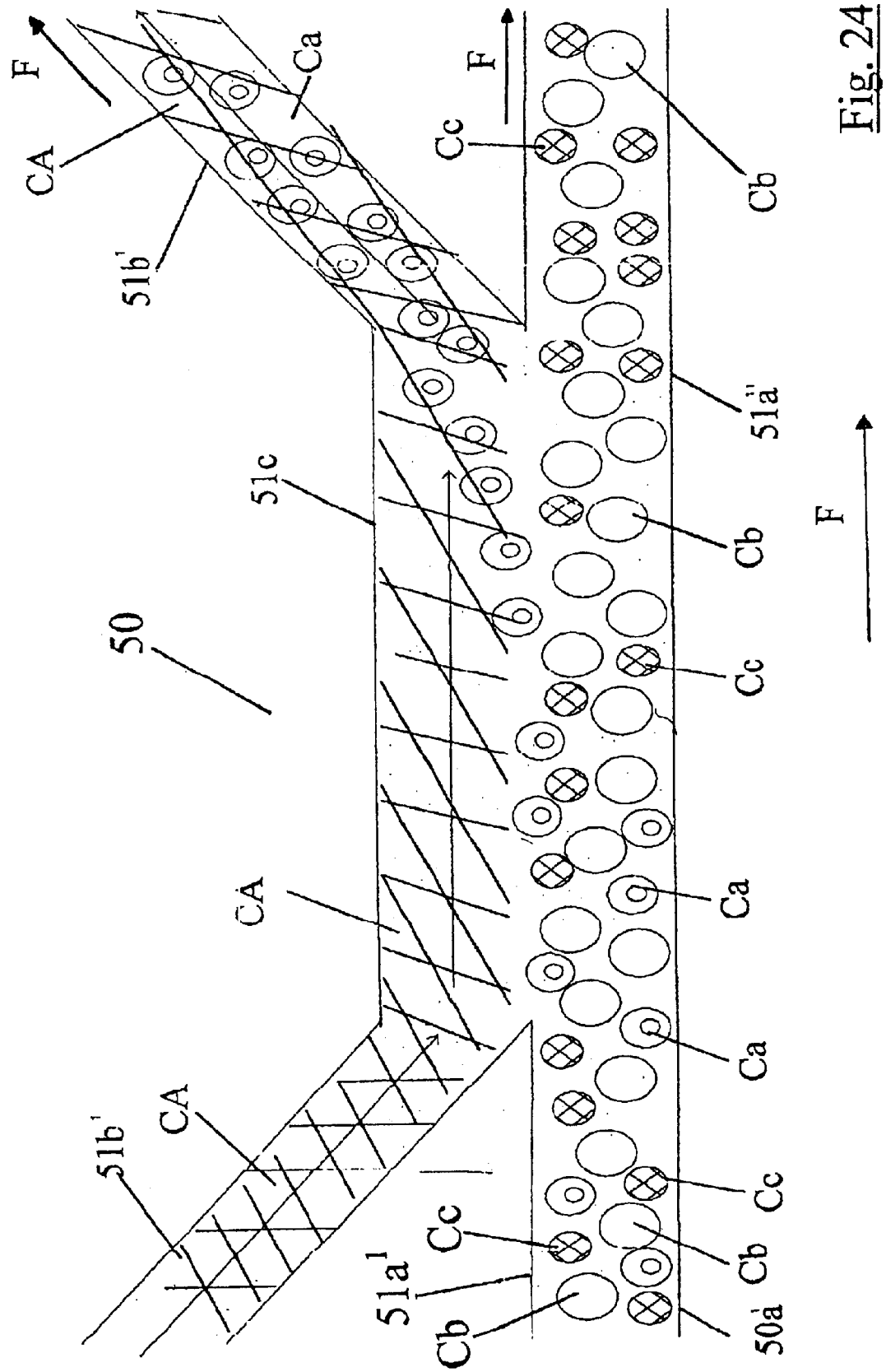
FIG. 24 is an enlarged view of portion of another biochip according to the invention.

Referring to FIG. 24, there is illustrated portion of a biochip again indicated by the reference numeral 50, having microchannels again all identified by the reference numeral 51 and subscript letters. The biochip comprises a main microchannel 51(*a*); feeder microchannels 51(*b*) and 51(*c*); and take-off microchannels 51(*d*) and 51(*e*). The sample liquid contains three cell types, namely, C(a), C(b) and C(c). In use, chemoattractant having an affinity with cells C(a) is fed through the feeder microchannel 51(*b*) to establish multilaminar flow with the sample liquid. The cells C(a) migrate into the chemoattractant and out the take-off microchannel 51(*b*) with the chemoattractant. This can be repeated as often as necessary. Further, many ways of take-off of the chemoattractant may be provided.

Needless to say, as in previous embodiments, it is possible to incorporate several interconnecting channels which allows the analysis of several different cell types interacting with several different drugs or chemoattractants. Also, following the analysis of the interaction between the drug or chemoattractant and the cell type, it is possible to coat the microchannel walls with individual specific ECM ligands, and so on. In other words, the variations of the tests already described may also be carried out with this arrangement.

Figure 25:
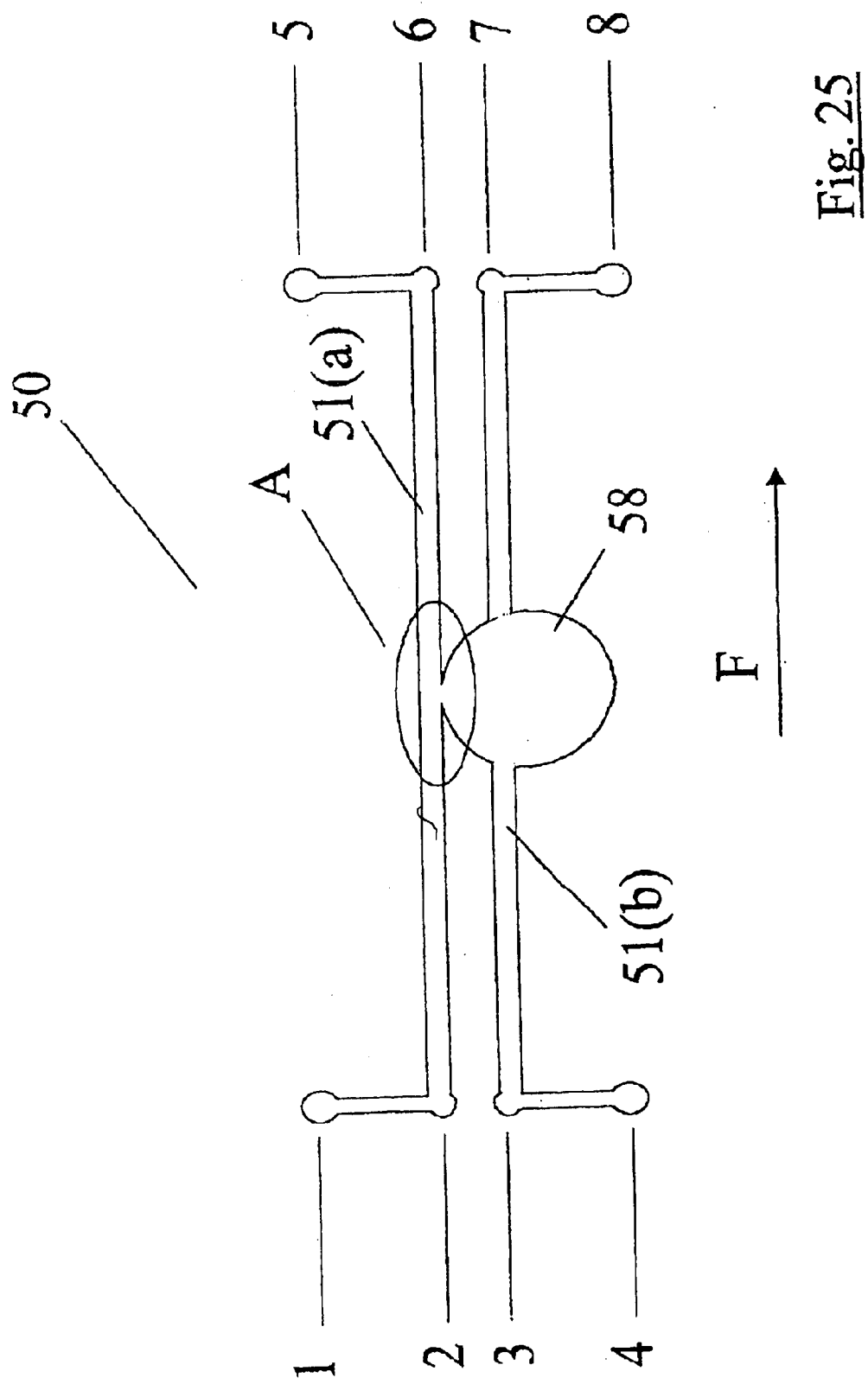
FIG. 25 is a plan view of a further biochip according to the invention.
Figure 26:
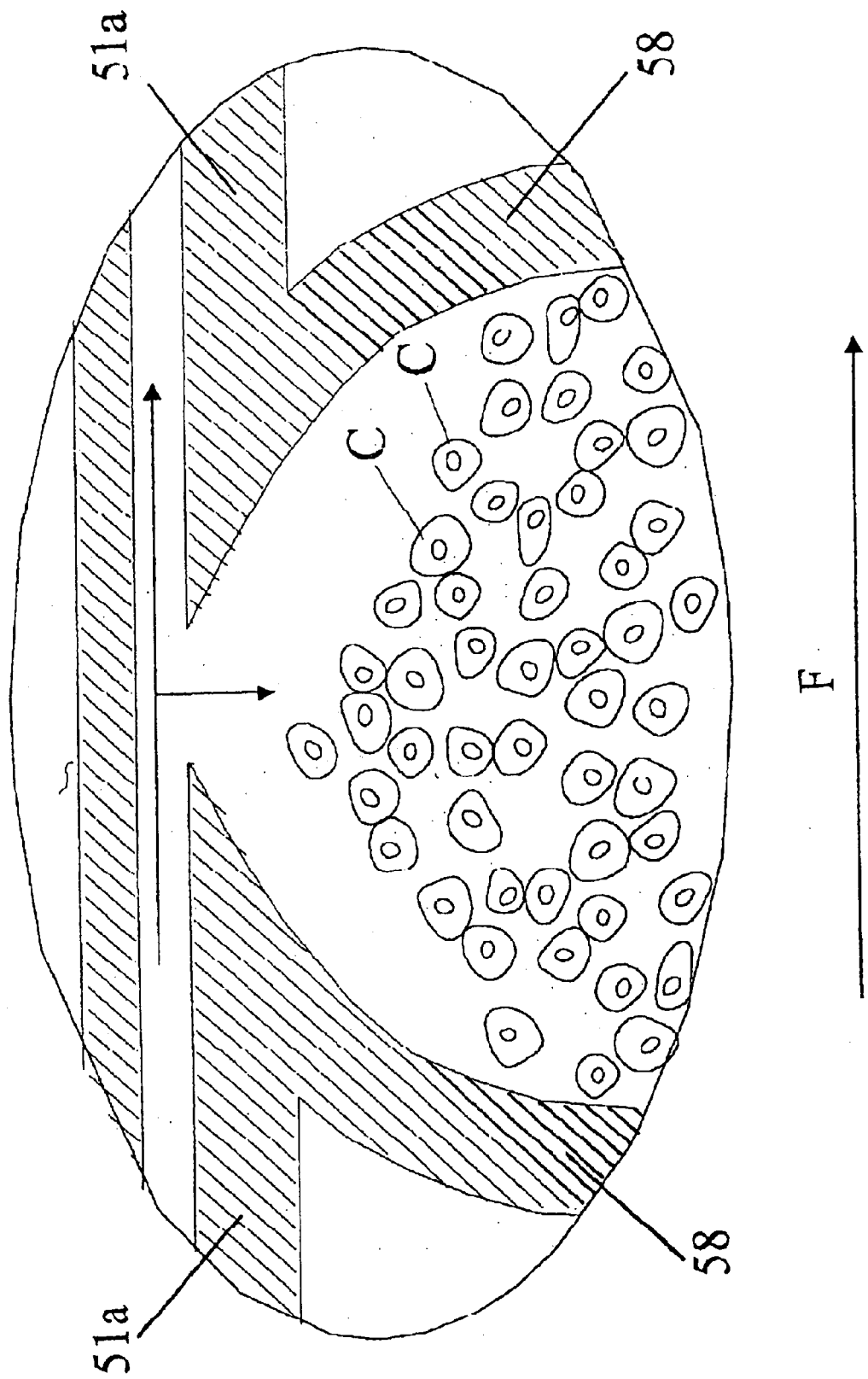
FIG. 26 is an enlarged view of a portion of the biochip identified by the reference letter A in FIG. 25.

Referring now to FIGS. 25 and 26, there is illustrated another construction of biochip again indicated generally by the reference numeral 50, in which parts similar to those described with reference to the previous drawings are identified by the same reference numerals. The biochip 59 has two microchannels which are identified by subscript letters (a) and (b) and the numeral 51.

There is a main microchannel 51(*a*) which has an inlet port 2 and an outlet port 6. There is connected a microwell 58 intermediate the ends of the main microchannel 51(*a*). A further microchannel 51(*b*) having an inlet port 3 adjacent its proximal end and an outlet port 7 adjacent its distal end, feeds the microwell 58.

In use, a sample liquid, again a culture medium containing cells C, is stored in the microwell 59 and a suitable culture medium or feed is delivered through the inlet port 3 through the microchannel 51(*b*) and then out from the microwell 59 through the outlet port 7. This culture medium is constantly flowing through the microwell 59 in order to feed the cells. In the upper channel 51(*a*), a drug and/or chemoattractant and/or toxic sample is delivered through the inlet port 2 through the microchannel 51(*a*) and out the outlet port 6. The pressure of the fluid flow in the upper microchannel 51(*a*) is slightly greater than in the microchannel 51(*b*) and thus there is a slow diffusion of the drug or the chemoattractant or the toxic sample into the microwell 59. This assay enables the study of the behaviour of the cells, for example, migration towards or away from the particular drug or chemoattractant or possibly the detrimental or even stimulating effects on the cells due to the introduction of the proposed toxic sample or reagent. This would be a very good way for testing the toxicity of drugs. Similarly, if a chemoattractant were introduced during the culture and growth of the cell type, it would determine the effect, if any, on its growth. Again, it is possible to coat the microchannel walls and the microwell walls with individual specific ECM ligands or endothelium layer. Again, several interconnecting channels may be coated with different ECM ligands facilitating the contemporaneous analysis of one or more cell types or chemoattractant drugs. Again, it will be appreciated that the biochip 58 could form part of a larger assay assembly.

One of the great advantages of using the biochips in accordance with the present invention is the reduction in reagent or sample consumption. It will also allow reduced analysis times and larger transfer rates due to the diminished distances involved. Additionally, in running several assays in parallel, each process in an assay can be manipulated step by step through computer control enabling great efficiency. Again, this accuracy in combination with higher yields, leads to a reduction in waste. This is not only more economically favourable but also environmentally beneficial where hazardous chemicals are involved.

In addition to chemical production, there are numerous other fields in which the micro devices according to the present invention can make a contribution, such as microbiology, pharmacy, medicine, biotechnology and environmental and materials science. The present invention is particularly adapted to the field of drug discovery and combinatorial chemistry. Again, there should be considerable cost savings for pharmaceutical companies. One of the great advantages of the present invention is that it mimics in vivo testing. Obviously, with the present invention, there is a constant flow of cells and the drug candidate, together with the micro capillary under observation, produces much more accurate statistical results.

One of the problems with current toxicity tests is that the systems implemented are not always representative of those in vivo providing results which are not characteristic of the in vivo situation. Secondly, there are differences with culturing and maintaining certain cells in vitro. The present invention allows one to simulate in vivo conditions eliminating many of the disadvantages of the present testing and hence immediately decreasing the necessity for animal trials while simultaneously increasing the statistical response as a result of the continuous flow assay according to the present invention.

One of the major problems with all drug testing is that clinical trials involve testing of the new drug in humans and because of the rigorous testing involved in a new drug, the time and cost of bringing a drug to market is enormous. It is for this reason that pharmaceutical companies must be extremely accurate with results obtained through experimental assays before presenting a new drug for clinical trials.

One of the advantages of the present invention is that relatively small volumes of blood can be used for analysis in hospitals which can be extremely advantageous. A particular advantage of the present invention is that the biochips are disposable.

The present invention essentially provides techniques for performing assays that test the interaction of a large number of chosen compounds, for example, candidate drugs or suspected toxic samples with living cells while the cells and/or the compounds mimic the in vivo situation of continuous flow. The assays according to the present invention imitate as far as possible the natural situation, while additionally overcoming the disadvantages of other techniques resulting in a fast and accurate process.

It will be appreciated that since the biochips are fabricated from a plastics material, it is considerably less expensive than, for example, silicone micro-machining which is often used at present, for such microchips.

One of the great advantages of plastics material is that it enables real-time monitoring with relative ease, by use of a inverted microscope.

The size of the microchannels is also significant. Dimensions below the order of 1 mm have long be avoided due to the many difficulties that occurred when scaling down. Such difficulties involve the control of flow within these microchannels.

While in the present invention, many tests have been tried and described, it will be appreciated that many other assays and tests can be carried out in accordance with the present invention. Indeed, some of the tests according to the present invention are not so much tests, as indeed filtering operations.

In the specification the terms "comprise, comprises, comprised and comprising" or any variation thereof and the terms "include, includes, included and including" or any variation thereof are considered to be totally interchangeable and they should all be afforded the widest possible interpretation.

The invention is not limited to the embodiments hereinbefore described but may be varied in both construction and detail.

What is claimed is:

1. A biological assay method for measuring cell flow, rolling, binding, tethering, migration of previously adhered cells, and/or adhesion comprising:
   preparing a sample liquid of a suspension of animal cells;
   coating the internal bore of a biochip with a protein, the biochip comprising an elongate enclosed microchannel having a bore substantially the same size as post capillary venules of the animal;
   delivering the sample liquid at a controlled steady flow rate through the microchannel; and
   measuring cell flow, rolling, binding, tethering, migration of previously adhered cells, and/or adhesion.

2. The biological assay method according to claim 1, further comprising coating the internal bore of the biochip with a protein in the form of an extracellular matrix ligand.

3. The biological assay method according to claim 1, further comprising:
   coating the internal bore of the biochip by seeding the biochip with endothelial cells; and
   allowing the cells to grow and form an endothelial layer on the bore.

4. The biological assay method according to claim 1, wherein the cells are taken from an animal and the bore of the biochip is substantially the same size as the post capillary venules of the animal.

5. The biological assay method according to claim 1, comprising delivering a reagent liquid at a controlled steady flow rate through another microchannel connected to the other microchannel, the channels being connected intermediate their ends by an interconnecting channel.

6. The biological assay method according to claim 1, further comprising delivering a reagent liquid at a controlled steady flow rate through another microchannel connected to the other microchannel, the channels being connected intermediate their ends by an interconnecting channel, the fluid pressure of the liquids being so chosen as to cause a diffusion of the reagent through the interconnecting channel and into the sample liquid.

7. The biological assay method according to claim 1, further comprising delivering a reagent liquid at a controlled steady flow rate through another microchannel connected to the other microchannel, the channels being connected intermediate their ends by an interconnecting channel, and the fluid pressures of the liquids are maintained equal to prevent diffusion of the reagent through the interconnecting channel.

8. The biological assay method according to claim 1, further comprising delivering a reagent liquid at a controlled steady flow rate through another microchannel connected to the other microchannel, the channels being connected intermediate their ends by an interconnecting channel having a restricted entry throat.

9. The biological assay method according to claim 1, further comprising delivering a reagent liquid at a controlled steady flow rate through another microchannel connected to the other microchannel, the channels being connected intermediate their ends by an interconnecting channel having a restricted entry throat, the fluid pressure of the liquids being so chosen as to cause a diffusion of the reagent through the interconnecting channel and into the sample liquid.

10. The biological assay method according to claim 1, further comprising delivering a reagent liquid at a controlled steady flow rate through another microchannel connected to the other microchannel, the channels being connected intermediate their ends by an interconnecting channel having a restricted entry throat and the fluid pressures of the liquids are maintained equal to prevent diffusion of the reagent through the interconnecting channel.

11. The biological assay method according to claim 1, further comprising delivering a reagent liquid at a controlled steady flow rate through another microchannel connected to the other microchannel, the channels being connected intermediate their ends by an interconnecting channel having a restricted entry throat having a cross-section less than that of a cell freely suspended in the sample liquid.

12. The biological assay method according to claim 1, further comprising delivering a reagent liquid at a controlled steady flow rate through another microchannel connected to the other microchannel, the channels being connected intermediate their ends by an interconnecting channel having a restricted entry throat having a cross-section less than that of a cell freely suspended in the sample liquid, the fluid pressure of the liquids being so chosen as to cause a diffusion of the reagent through the interconnecting channel and into the sample liquid.

13. The biological assay method according to claim 1, further comprising delivering a reagent liquid at a controlled steady flow rate through another microchannel connected to the other microchannel, the channels being connected intermediate their ends by an interconnecting channel having a restricted entry throat having a cross-section less than that of a cell freely suspended in the sample liquid and the fluid pressures of the liquids are maintained equal to prevent diffusion of the reagent through the interconnecting channel.

14. The biological assay method according to claim 1, further comprising coating the bore of the microchannel with a hydrophobic coating and delivering a reagent liquid through the microchannel with the sample liquid.

15. The biological assay method according to claim 1, further comprising coating the bore of the microchannel with a liquid silicone and delivering a reagent liquid through the microchannel with the sample liquid.

16. The biological assay method according to claim 1, wherein the sample liquid contains more than one cell type in suspension.

17. The biological assay method according to claim 1, further comprising delivering a reagent liquid at a controlled steady flow rate through another microchannel connected to the other microchannel, the channels being connected intermediate their ends by an interconnecting channel having a restricted entry throat having a cross-section less than that of a cell freely suspended in the sample liquid.

18. The biological assay method according to claim 1, further comprising delivering a reagent liquid at a controlled steady flow rate through another microchannel connected to the other microchannel, the channels being connected intermediate their ends by an interconnecting channel having a restricted entry throat having a cross-section less than that of a cell freely suspended in the sample liquid, the fluid pressure of the liquids being so chosen as to cause a diffusion of the reagent through the interconnecting channel and into the sample liquid.

19. The biological assay method according to claim 1, further comprising delivering a reagent liquid at a controlled steady flow rate through another microchannel connected to the other microchannel, the channels being connected intermediate their ends by an interconnecting channel having a restricted entry throat having a cross-section less than that of a cell freely suspended in the sample liquid and the fluid pressures of the liquids are maintained equal to prevent diffusion of the reagent through the interconnecting channel.

20. The biological assay method according to claim 1, further comprising coating the bore of the microchannel with a hydrophobic coating and delivering a reagent liquid through the microchannel with the sample liquid.

21. The biological assay method according to claim 1, further comprising coating the bore of the microchannel with a liquid silicone and delivering a reagent liquid through the microchannel with the sample liquid.

22. The biological assay method according to claim 1, wherein the sample liquid contains more than one cell type in suspension.

23. The biological assay method according to claim 1, further comprising delivering a reagent liquid and the sample liquid through the microchannel to form multilaminar flow.

24. The biological assay method according to claim 1, further comprising:
    delivering a reagent liquid and a sample through a microchannel to form multilaminar flow, the sample liquid comprising more than once cell type in suspension and the reagent liquid comprising a chemoattractant suitable for one of the types of cell;
    allowing the flow to continue sufficiently so as to remove that cell type into the reagent liquid; and separating the reagent liquid and the sample liquid.

25. The biological assay method according to claim 1, wherein the biochip comprises two microchannels, one a feeding microchannel having a cell reservoir intermediate its ends and the other a reactant microchannel connected to the reservoir by a connecting means comprising:
    storing cells in the cell reservoir;
    feeding and growing the cells in the cell reservoir by delivering a culture medium through the feeding microchannel; and
    delivering liquid through the reactant microchannel.

26. The biological assay method according to claim 1, wherein the biochip comprises two microchannels, one a feeding microchannel having a cell reservoir intermediate its ends and the other a reactant microchannel connected to the reservoir by a connecting means comprising:
    storing cells in the cell reservoir;
    feeding and growing the cells in the cell reservoir by delivering a culture medium through the feeding microchannel; and
    delivering a reagent chosen from one or more of a chemoattractant toxic substance and pharmaceutical preparation recombinant or cell derived through the reactant microchannel.

27. The biological assay method according to claim 1, wherein a plurality of tests are carried out simultaneously using a sample liquid forming portion of a larger sample and using different test conditions.

28. The biological assay method according to claim 1, wherein a plurality of tests are carried out simultaneously using different sample liquids and the same test conditions.

29. A transmigration assay method to determine cell migration from the endothelium to the extracellular matrix comprising:
    delivering a sample liquid comprising a suspension of cells at a controlled steady flow rate through a microchannel forming a biochip with an internal bore;
    delivering a chemoattractant through another microchannel forming the biochip and being connected to the other microchannel through a restricted entry of size less than that of a freely suspended cell; and
    observing the migration of cells through the restricted entry to the chemoattractant.

30. The transmigration method according to claim 29, further comprising coating the internal bore of the biochip with a protein.

31. The transmigration method according to claim 29, further comprising coating the internal bore of the biochip with a protein in the form of an extracellular matrix ligand.

32. The transmigration method according to claim 29, further comprising:

coating the internal bore of the biochip by seeding the biochip with an endothelial cells; and allowing the cells to grow and form an endothelial layer on the bore.

33. The transmigration method according to claim 29, wherein the fluid pressure of the liquids is so chosen as to provide a diffusion of the sample liquid through the restricted entry.

34. The transmigration method according to claim 29, wherein the fluid pressures of the liquids are the same.

35. The transmigration method according to claim 29, wherein a plurality of tests are carried out simultaneously using a sample liquid forming portion of a larger sample and using different test conditions.

36. A method of separating a cell type from a sample liquid containing at least another cell type comprising:

delivering a chemoattractant and the sample liquid through a microchannel forming part of a biochip, the liquids forming multilaminar flow and the chemoattractant having an affinity to the cell type allowing the flow to continue sufficiently so as to remove that cell type into the chemoattractant; and subsequently separating the chemoattractant liquid and the sample liquid.

37. A method of separating a cell type from a sample liquid containing at least another cell type comprising:

delivering a chemoattractant and the sample liquid through a microchannel forming part of a biochip, the liquids forming multilaminar flow and the chemoattractant having an affinity to the cell type allowing the flow to continue sufficiently so as to remove that cell type into the chemoattractant; and subsequently separating the chemoattractant liquid and the sample liquid.

38. The method according to claim 37, wherein a plurality of tests are carried out simultaneously using a sample liquid forming portion of a larger sample and using different test conditions.

39. The method according to claim 37, wherein a plurality of tests are carried out simultaneously using different sample liquids and the same test conditions.

* * * * *